US005723398A

United States Patent [19]

Rosen et al.

[11] Patent Number: 5,723,398
[45] Date of Patent: Mar. 3, 1998

[54] HOMOGENEOUS, STABILIZED, REDUCED METAL ADDITION POLYMERIZATION CATALYSTS, PROCESS FOR PREPARATION AND METHOD OF USE

[75] Inventors: Robert K. Rosen, Sugar Land, Tex.; Peter N. Nickias, Midland, Mich.; David D. Devore, Midland, Mich.; James C. Stevens, Midland, Mich.; Francis J. Timmers, Midland, Mich.

[73] Assignee: The Dow Chemical Company, Midland, Mich.

[21] Appl. No.: 498,964

[22] Filed: Jul. 6, 1995

Related U.S. Application Data

[62] Division of Ser. No. 294,469, Aug. 23, 1994, Pat. No. 5,494,874, which is a division of Ser. No. 8,003, Jan. 21, 1993, Pat. No. 5,374,696, which is a continuation-in-part of Ser. No. 941,014, Sep. 4, 1992, abandoned, which is a continuation-in-part of Ser. No. 857,886, Mar. 26, 1992, abandoned.

[51] Int. Cl.$^6$ .................... B01J 31/00; B01J 37/00; C08F 4/02; C08F 4/60
[52] U.S. Cl. .................. 502/103; 502/117; 502/118; 502/152; 502/155; 502/158; 526/160; 526/943; 556/53
[58] Field of Search ...................... 502/103, 117, 502/118, 152, 155, 158

[56] References Cited

U.S. PATENT DOCUMENTS

| | | | |
|---|---|---|---|
| 4,057,565 | 11/1977 | Manzer | 526/159 |
| 4,870,042 | 9/1989 | Kohara et al. | 502/114 |
| 5,064,802 | 11/1991 | Stevens et al. | 502/155 |
| 5,189,192 | 2/1993 | LaPointe et al. | 556/11 |
| 5,321,106 | 6/1994 | LaPointe | 526/126 |
| 5,374,696 | 12/1994 | Rosen et al. | 502/155 |
| 5,494,874 | 2/1996 | Rosen et al. | 502/155 |
| 5,532,394 | 7/1996 | Rosen et al. | 556/11 |
| 5,565,396 | 10/1996 | Frey et al. | 502/117 |

FOREIGN PATENT DOCUMENTS

| | | |
|---|---|---|
| 0 416 815 | 3/1991 | European Pat. Off. . |
| 0 427 697 | 5/1991 | European Pat. Off. . |
| 0 468 537 | 1/1992 | European Pat. Off. . |
| 0 468 651 | 1/1992 | European Pat. Off. . |
| 0 495 375 | 7/1992 | European Pat. Off. . |

OTHER PUBLICATIONS

J. Okuda, Chem.Ber., vol. 123, pp. 1649–1651 1990.

J.J. Eisch et al., J. Organomet. Chem., vol. 334, pp. C1–C4 1987.

L. Manzer, J.Am.Chem.Soc., vol. 100, No. 26, pp. 8068–8073 Dec. 1978.

T.J. Marks et al., J.Am.Chem.Soc., vol. 113, pp. 3623–3625 1991.

J.H. Teuben et al., Organometallics, vol. 10, No. 9, pp. 3227–3237 Sep. 1991.

*Primary Examiner*—Glenn Caldarola
*Assistant Examiner*—J. Pasterczyk

[57] ABSTRACT

Addition polymerization catalysts-comprising 1) a Group 4 metal complex in the $^+3$ oxidation state containing two delocalized π-bonding moieties, and a stabilizing ligand covalently bonded to the metal and also datively bonded to the metal via lone pair electrons of an amine, phosphine, ether or thioether group and 2) an activating cocatalyst.

7 Claims, No Drawings

HOMOGENEOUS, STABILIZED, REDUCED METAL ADDITION POLYMERIZATION CATALYSTS, PROCESS FOR PREPARATION AND METHOD OF USE

CROSS-REFERENCE TO RELATED APPLICATION

This is a divisional of Ser. No. 08/294,469, filed Aug. 23, 1994, now U.S. Pat. No. 5,494,874, which was a divisional of Ser. No. 08/008,003, filed Jan. 21, 1993, now U.S. Pat. No. 5,374,696, which was a continuation-in-part of application Ser. No. 07/941,014, filed Sep. 4, 1992, now abandoned which is a continuation-in-part of application Ser. No. 07/857,886, filed Mar. 26, 1992, now abandoned, the teachings of which are hereby incorporated by reference.

BACKGROUND OF THE INVENTION

This invention relates to the use of catalysts comprising certain stabilized, reduced metal complexes in the polymerization of olefin polymers. In one embodiment such catalysts additionally employ an activating cocatalyst. In another embodiment such catalysts may be employed with or without an activating cocatalyst. Finally the invention relates to an improved method for preparing the stabilized reduced metal complexes. The compositions are especially useful as catalysts for the polymerization of olefins such as ethylene for polymers having utility as molding resins and in the formation of foamed products having cushioning and insulating applications and films that are useful as protective wrappings.

In U.S. Ser. No. 545,403, filed Jul. 3, 1990 (equivalent to EP-A-416,845) there are disclosed and claimed certain monocyclopentadienyl metal complexes having utility as homogeneous olefin polymerization catalysts. In U.S. Pat. No. 5,064,802 (equivalent to EP-A-418,044), cationic monocyclopentadienyl metal complexes with salts of Bronsted acids containing a non-coordinating compatible anion are disclosed and claimed. Finally, in U.S. Ser. No. 547,718, also filed on Jul. 3, 1990 (EP-A-468,651), an oxidative activation technique for preparing such cationic catalysts is disclosed and claimed. For the teachings contained therein the above mentioned pending U.S. applications and U.S. patent are herein incorporated in their entirety by reference thereto.

In *J. Am. Chem. Soc.* 113, 3623–3625 (1991) there is disclosed a process for preparation of "cation like" zirconocene polymerization complexes by alkyl abstraction using tris(pentafluorophenyl)borane. The complexes were stated to have activity roughly comparable to typical complexes employing alumoxane. No suggestion as to the suitability of the disclosed technique for use with reduced oxidation state metal catalysts is provided by the reference.

In U.S. Pat. No. 4,057,565 there are disclosed Ti, Zr, or Hf derivatives of 2-dialkylaminobenzyl or 2-dialkylaminomethylphenyl all in the +4 oxidation state which are useful as components of catalysts for olefin polymerization. No mention is given for +3 oxidation state metal catalysts.

In *J. Am. Chem. Soc.* 100, 8068–8073 (1978) there is mentioned the synthesis and characterization of Ti(+3) complexes containing cyclopentadienyl groups and 2-dialkylaminobenzyl or 2-dialkylaminomethylphenyl groups. No mention of utility as addition polymerization catalysts is given.

In U.S. Pat. No. 4,870,042, catalysts for olefin polymerizations comprising a pyrazolyl borate complex of titanium or zirconium compounds including titanium trichloride (Example 4) are disclosed.

In *Organometallics*, 10, 3227–3237 (1991) certain titanium +3 complexes containing cyclopentadienyl groups and alkyl groups are mentioned. On page 3236, the reference states:

"So far no well-defined neutral titanium-based molecular system with established activity for catalytic olefin polymerization has been described . . . Apparently, the tervalent Cp*₂TiR system cannot induce sufficient positive charge at the β-carbon atom of an incoming ethylene molecule to reach the polar transition state for migratory insertion."

In *Journal of Organometallic Chemistry*, 334 (1987) C1–C4, η³-allyl(bis-η⁵-cyclopentadienyl)titanium (III) activated with dimethylaluminum chloride was found to create a coordinated species Cp₂Ti (allyl) —(CH₃)₂AlCl which was found to polymerize ethylene. Use of stronger Lewis acids so as to cause ligand abstraction thereby destroying the requisite carbon-titanium bond was to be avoided according to the reference.

In accordance with the present invention there is provided an addition polymerization catalyst comprising in combination:

a metal complex, $A_1$, corresponding to the formula $$Cp_2ML, \quad \text{(Ia)}$$

wherein

Cp independently each occurrence is a cyclopentadienyl group η-bound to M, or a hydrocarbyl, silyl, halo, halohydrocarbyl, hydrocarbylmetalloid or halohydrocarbylmetalloid substituted derivative of said cyclopentadienyl group, said Cp containing up to 50 nonhydrogen atoms, and optionally both Cp groups may be joined together by a bridging group;

M is a metal of Group 4 of the Periodic Table of the Elements in the +3 oxidation state;

L is a monovalent anionic stabilizing ligand selected from the group consisting of: alkyl, cycloalkyl, aryl, silyl, amido, phosphido, alkoxy, aryloxy, sulfido groups and mixtures thereof, and being further substituted with an amine, phosphine, ether, or thioether containing substituent able to form a coordinate-covalent bond or chelating bond with M; said ligand having up to 50 nonhydrogen atoms;

and an activating cocatalyst.

Preferably in accordance with the present invention the ratio of metal complex to activating cocatalyst is from 1:0.01 to 1:10⁶.

In a further embodiment there is provided an addition polymerization catalyst comprising in combination:

a metal complex, $A_2$, corresponding to the formula $$Cp'ML'_2, \quad \text{(Ib)}$$

wherein

Cp' is a cyclopentadienyl group, or a hydrocarbyl, silyl, halo, halohydrocarbyl, or hydrocarbylmetalloid substituted derivative thereof, said Cp' containing up to 50 nonhydrogen atoms;

M is a metal of Group 4 of the Periodic Table of the Elements in the ⁺3 oxidation state;

L' independently each occurrence is hydride, halo, or a monovalent anionic ligand selected from the group consisting of hydrocarbyl, silyl, amido, phosphido, alkoxy, aryloxy, and sulfido groups; mixtures thereof; and amine, phosphine, ether, and thioether derivatives of the foregoing, said ligand having up to 50 nonhydrogen atoms, with the proviso that in at least one occurrence L' is a stabilizing ligand comprising an amine, phosphine, ether or thioether functionality able to form a coordinate-covalent bond or chelating bond with M, or comprising an ethylenic unsaturation able to form an η3 bond with M;

and an activating cocatalyst.

Preferably the activating cocatalyst is present in an amount to provide a ratio of metal complex to activating cocatalyst from 1:0.01 to 1:10$^6$.

In a still further embodiment of the present invention there is provided a metal complex, A$_3$, corresponding to the formula:

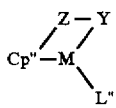
(Ic)

wherein

M is a metal of Group 4 of the Periodic Table of the Elements in the $^+3$ oxidation state;

Cp" is a cyclopentadienyl group, or a hydrocarbyl, silyl, halo, halohydrocarbyl, or hydrocarbylmetalloid substituted derivative thereof, said Cp' containing up to 50 nonhydrogen atoms;

Z is a divalent moiety comprising oxygen, nitrogen, phosphorous, boron, or a member of Group 14 of the Periodic Table of the Elements said moiety having up to 30 nonhydrogen atoms;

Y is a linking group comprising nitrogen, phosphorus, oxygen or sulfur covalently bonded to M and Z through said nitrogen, phosphorus, oxygen or sulfur atom, the ligand moiety consisting of —Cp"—Z—Y— being dianionic and having the ionic charges residing formally on Cp" and Y; and L" is a stabilizing ligand selected from the group consisting of L and C$_{3-10}$ hydrocarbyl groups comprising an ethylenic unsaturation able to form an η3 bond with M.

The above complexes, A$_3$, are suitable for use in polymerization of addition polymerizable monomers alone or optionally in the presence of an activating cocatalyst. When present, the activating cocatalyst is preferably used in an amount to provide a ratio of metal complex to activating cocatalyst from 1:0.01 to 1:10$^6$.

DETAILED DESCRIPTION

The metal complexes, A$_1$, may be prepared by a process comprising contacting a Group 4 metal complex corresponding to the formula:

Cp$_2$M*XL (IIa)

wherein Cp and L are as previously defined, and

M* is a metal of Group 4 of the Periodic Table of the Elements in the $^+4$ oxidation state; and X is halide or C$_{1-10}$ hydrocarbyloxide, with a reducing agent under reducing conditions to form the Group 4 metal complex.

The metal complexes, A$_2$, may be prepared by a process comprising contacting a Group 4 metal complex corresponding to the formula:

Cp'M*XL'$_2$ (IIb)

wherein Cp' and L' are as previously defined, and

M* is a metal of Group 4 of the Periodic Table of the Elements in the $^+4$ oxidation state; and X is halide or C$_{1-10}$ hydrocarbyloxide, with a reducing agent under reducing conditions to form the Group 4 metal complex.

Finally, the metal complexes, A$_3$, may be prepared by a process comprising contacting a Group 4 metal complex corresponding to the formula:

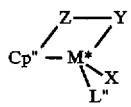
IIc wherein Cp", Z, Y, M*, X and L" are as previously defined, with a reducing agent under reducing conditions to form the Group 4 metal complex.

There are also provided olefin polymerization processes comprising a polymerizable olefin or mixture thereof with the foregoing catalysts under polymerization conditions and recovering the resulting polymer.

All reference to the Periodic Table of the Elements herein shall refer to the Periodic Table of the Elements, published and copyrighted by CRC Press, Inc., 1989. Also, any reference to a Group or Groups shall be to the Group or Groups as reflected in this Periodic Table of the Elements using the IUPAC system for numbering groups.

By the term "stabilizing ligand" is meant that the ligand group stabilizes the metal complex through either:

1) a nitrogen, phosphorus, oxygen or sulfur chelating bond, or 2) an η$^3$ bond with a resonant, delocalized n-electronic structure.

Examples of stabilizing ligands of group 1) for use according to the present invention include silyl, hydrocarbyl, amido or phosphido ligands substituted with one or more aliphatic or aromatic ether-, thioether, amine or phosphine functional groups, especially such amine or phosphine groups that are tertiary substituted, said stabilizing ligand having from 3 to 30 nonhydrogen atoms. Most preferred group 1) stabilizing ligands are 2-dialkylaminobenzyl or 2-(dialkylaminomethyl)phenyl groups containing from 1 to 4 carbons in the alkyl groups.

Examples of stabilizing ligands of group 2) for use according to the present invention, include C$_{3-15}$ hydrocarbyl groups containing ethylenic unsaturation, such as allyl, 1-methylallyl, 2-methylallyl, 1,1-dimethylallyl, or 1,2,3-trimethylallyl groups.

Preferred substituents of the groups Cp, Cp' and Cp" are hydrocarbyl, hydrocarbylene, halosubstituted hydrocarbyl groups having from 1 to 30 carbons, and C$_{1-30}$ hydrocarbyl or halohydrocarbyl substituted metalloid radicals wherein the metalloid is an element from Group 14 of the Periodic Table of the Elements.

Exemplary hydrocarbyl radicals include straight and branched alkyl radicals, cyclic aliphatic hydrocarbon radicals, alkyl-substituted cyclic aliphatic hydrocarbon radicals, aromatic radicals and alkyl-substituted aromatic radicals. Preferred are methyl, ethyl, butyl and phenyl radicals. Exemplary organo-metalloid radicals include straight and branched chain silyl radicals, alkyl-substituted silyl radicals, germyl radicals and divalent derivatives of the foregoing. Preferred are trimethylsilyl, triethylsilyl, ethyldimethylsilyl, methyldiethylsilyl, dimethyl-t-butylsilyl, triphenylsilyl, triphenylgermyl, and trimethylgermyl radicals.

More particularly, suitable cyclopentadienyl or substituted cyclopentadienyl groups in complexes $A_1$ are illustrated by the formula:

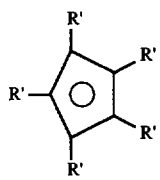
(III)

wherein

R' is hydrogen, or a group selected from silyl, hydrocarbyl, and combinations thereof having up to 30 carbon or silicon atoms, or two R' groups together form a divalent derivative of such group.

Preferably, R' independently each occurrence is hydrogen, methyl, ethyl, propyl, butyl, pentyl, hexyl, (including where appropriate all isomers), cyclopentyl, cyclohexyl, norbornyl, benzyl, or phenyl or two R' groups are linked together thereby forming an indenyl, tetrahydroindenyl, fluorenyl, tetrahydrofluorenyl, or octahydrofluorenyl group in place of the cyclopentadienyl group.

Exemplary metal complexes of formula $A_1$ are: bis (methylcyclopentadienyl)titanium 2-dimethylaminobenzyl, bis(methylcyclopentadienyl)titanium 2-dimethylaminomethylphenyl, bis(ethylcyclopentadienyl) titanium 2-dimethylaminobenzyl, bis (ethylcyclopentadienyl)titanium 2-dimethylaminomethylphenyl, bis(n-butylcyclopentadienyl)titanium 2-dimethylaminobenzyl, bis (t-butylcyclopentadienyl)titanium 2-dimethylaminobenzyl, bis(n-butylcyclopentadienyl)titanium 2-dimethylaminomethylphenyl, bis(t-butylcyclopentadienyl)titanium 2-dimethylaminomethylphenyl, bis (pentamethylcyclopentadienyl)titanium 2-dimethylaminobenzyl, bis(pentamethylcyclopentadienyl) titanium 2-dimethylaminomethylphenyl, bis(indenyl) 2-dimethylaminobenzyl, bis(indenyl)titanium 2-dimethylaminomethylphenyl, bis(fluorenyl) 2-dimethylaminobenzyl, bis(fluorenyl)titanium 2-dimethylaminomethylphenyl, bis(cyclopentadienyl) zirconium 2-dimethylaminobenzyl, bis(cyclopentadienyl) zirconium 2-dimethylaminomethylphenyl, bis (methylcyclopentadienyl)zirconium 2-dimethylaminobenzyl, bis(methylcyclopentadienyl) zirconium 2-dimethylaminomethylphenyl, bis (ethylcyclopentadienyl)zirconium 2-dimethylaminobenzyl, bis(ethylcyclopentadienyl)zirconium 2-dimethylaminomethylphenyl, bis(n-butyl cyclopentadienyl)zirconium 2-dimethylaminobenzyl, bis(t-butylcyclopentadienyl)zirconium 2-dimethylaminobenzyl, bis(n-butylcyclopentadienyl)zirconium 2-dimethylaminomethylphenyl, bis(t-butylcyclopentadienyl)zirconium 2-dimethylaminomethylphenyl, bis (pentamethylcyclopentadienyl)zirconium 2-dimethylaminobenzyl, bis (pentamethylcyclopentadienyl) zirconium 2-dimethylaminomethylphenyl, bis(indenyl) 2-dimethylaminobenzyl, bis (indenyl)zirconium 2-dimethylaminomethylphenyl, bis(fluorenyl) 2-dimethylaminobenzyl, bis(fluorenyl)zirconium 2-dimethylaminomethylphenyl, bis(cyclopentadienyl) hafnium 2-dimethylaminobenzyl, bis(cyclopentadienyl) hafnium 2-dimethylaminomethylphenyl, bis (methylcyclopentadienyl)hafnium 2-dimethylaminobenzyl, bis(methylcyclopentadienyl)hafnium 2-dimethylaminomethylphenyl, bis(ethylcyclopentadienyl) hafnium 2-dimethylaminobenzyl bis(ethylcyclopentadienyl) hafnium 2-dimethylaminomethylphenyl, bis (butylcyclopentadienyl)hafnium 2-dimethylaminobenzyl, bis(butylcyclopentadienyl)hafnium 2-dimethylaminomethylphenyl, bis (pentamethylcyclopentadienyl)hafnium 2-dimethylaminobenzyl, bis(pentamethylcyclopentadienyl) hafnium 2-dimethylaminomethylphenyl, bis(indenyl) 2-dimethylaminobenzyl, bis(indenyl)hafnium 2-dimethylaminomethylphenyl, bis(fluorenyl)hafnium 2-dimethylaminobenzyl, and bis(fluorenyl)hafnium 2-dimethylaminomethylphenyl.

Additional bis-cyclopentadienyl compounds of formula $A_1$ include those containing a bridging group linking the cyclopentadienyl groups. Preferred bridging groups are those corresponding to the formula $(ER''_2)_x$ wherein E is silicon or carbon, R'', independently each occurrence is hydrogen or a group selected from silyl, hydrocarbyl and combinations thereof, said R'' having up to 30 carbon or silicon atoms, and x is 1 to 8. Preferably R'' independently each occurrence is methyl, benzyl, tert-butyl, or phenyl.

Examples of the foregoing bridged cyclopentadienyl group containing complexes are compounds corresponding to the formula:

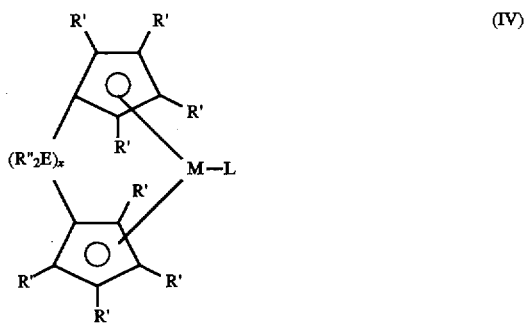
(IV)

wherein

M, L, E, R' R'' and x are as previously defined.

Such bridged structures are especially suited for the preparation of polymers having stereoregular molecular structure. In such capacity it is preferred that the complex be nonsymmetrical or possess a chiral, stereorigid structure. Examples of the first type are compounds possessing different delocalized n-bonded systems, such as one cyclopentadienyl group and one indenyl group. Similar systems based on Ti(IV) or Zr(IV) were disclosed for preparation of syndiotactic olefin polymers in Ewen, et al., J. Am. Chem. Soc. 110, 6255–6256 (1980). Examples of chiral structures bis-indenyl complexes. Similar systems based on Ti(IV) or Zr(IV) were disclosed for preparation of isotactic olefin polymers in Wild et al., J. Organomet. Chem, 232, 233–47, (982).

Exemplary bridged cyclopentadienyl complexes of formula Ia are: (dimethylsilyl-bis-cyclopentadienyl) titanium 2-dimethylaminobenzyl, (dimethylsilyl-bis-cyclopentadienyl) titanium 2-dimethylaminomethylphenyl, (dimethylsilyl-bis-methylcyclopentadienyl) titanium 2-dimethylaminobenzyl, (dimethylsilyl-bis-methylcyclopentadienyl) titanium 2-dimethylaminomethylphenyl, (dimethylsilyl-bis-ethylcyclopentadienyl)titanium 2-dimethylaminobenzyl, (dimethylsilyl-bis-ethylcyclopentadienyl) titanium 2-dimethylaminomethylphenyl, (dimethylsilyl-bis-n-butylcyclopentadienyl) titanium 2-dimethylaminobenzyl, (dimethylsilyl-bis-t-butylcyclopentadienyl) titanium 2-dimethylaminobenzyl, (dimethylsilyl-bis-n-butylcyclopentadienyl) titanium 2-dimethylaminomethylphenyl, (dimethylsilyl-bis-t-butylcyclopentadienyl) titanium 2-dimethylaminomethylphenyl, (dimethylsilyl-bis-tetramethylcyclopentadienyl) titanium 2-dimethylaminobenzyl, (dimethylsilyl-bis-tetramethylcyclopentadienyl) titanium 2-dimethylaminomethylphenyl, (dimethylsilyl-bis-indenyl) titanium 2-dimethylaminobenzyl, (dimethylsilyl-bis-indenyl) titanium 2-dimethylaminomethylphenyl, (dimethylsilyl-bis-tetrahydroindenyl) titanium 2-dimethylaminobenzyl, (dimethylsilyl-bis-tetrahydroindenyl) titanium 2-dimethylaminomethylphenyl, (dimethylsilyl-bis-fluorenyl) titanium 2-dimethylaminobenzyl, (dimethylsilyl-bis-fluorenyl) titanium 2-dimethylaminomethylphenyl, (dimethylsilyl-bis-tetrahydrofluorenyl) titanium 2-dimethylaminobenzyl, (dimethylsilyl-bis-tetrahydrofluorenyl) titanium 2-dimethylaminomethylphenyl, (dimethylsilylcyclopentadienyl-fluorenyl) titanium 2-dimethylaminobenzyl, (dimethylsilyl-cyclopentadienyl-fluorenyl) titanium 2-dimethylaminomethylphenyl, (isopropylidenecyclopentadienyl-fluorenyl) titanium 2-dimethylaminobenzyl, (isopropylidene-cyclopentadienyl-fluorenyl) titanium 2-dimethylaminomethylphenyl, (dimethylsilyl-bis-cyclopentadienyl) zirconium 2-dimethylaminobenzyl, (dimethylsilyl-bis-cyclopentadienyl) zirconium 2-dimethylaminomethylphenyl, (dimethylsilyl-bis-methylcyclopentadienyl) zirconium 2-dimethylaminobenzyl, (dimethylsilyl-bis-methylcyclopentadienyl) zirconium 2-dimethylaminomethylphenyl, (dimethylsilyl-bis-ethylcyclopentadienyl) zirconium 2-dimethylaminobenzyl, (dimethylsilyl-bis-ethylcyclopentadienyl) zirconium 2-dimethylaminomethylphenyl, (dimethylsilyl-bis-t-butylcyclopentadienyl) zirconium 2-dimethylaminobenzyl, (dimethylsilyl-bis-n-butylcyclopentadienyl) zirconium 2-dimethylaminomethylphenyl, (dimethylsilyl-bis-t-butylcyclopentadienyl) zirconium 2-dimethylaminomethylphenyl, (dimethylsilyl-bis-tetramethylcyclopentadienyl) zirconium 2-dimethylaminobenzyl, (dimethylsilyl-bis-tetramethylcyclopentadienyl) zirconium 2-dimethylaminomethylphenyl, (dimethylsilyl-bis-indenyl) zirconium 2-dimethylaminobenzyl, (dimethylsilyl-bis-indenyl) zirconium 2-dimethylaminomethylphenyl, (dimethylsilyl-bis-tetrahydroindenyl) zirconium 2-dimethylaminobenzyl, (dimethylsilyl-bis-tetrahydroindenyl) zirconium 2-dimethylaminomethylphenyl, (dimethylsilyl-bis-fluorenyl) zirconium 2-dimethylaminobenzyl, (dimethylsilyl-bis-fluorenyl) zirconium 2-dimethylaminomethylphenyl, (dimethylsilyl-bis-tetrahydrofluorenyl) zirconium 2-dimethylaminobenzyl, (dimethylsilyl-bis-tetrahydrofluorenyl) zirconium 2-dimethylaminomethylphenyl, (dimethylsilyl-cyclopentadienylfluorenyl) zirconium 2-dimethylaminobenzyl, (dimethylsilyl-cyclopentadienyl-fluorenyl) zirconium 2-dimethylaminomethylphenyl, (isopropylidenecyclopentadienyl-fluorenyl) zirconium 2-dimethylaminobenzyl, (isopropylidene-cyclopentadienylfluorenyl) zirconium 2-dimethylaminomethylphenyl, (dimethylsilyl-bis-cyclopentadienyl) hafnium 2-dimethylaminobenzyl, (dimethylsilyl-bis-cyclopentadienyl) hafnium 2-dimethylaminomethylphenyl, (dimethylsilyl-bis-methylcyclopentadienyl) hafnium 2-dimethylaminobenzyl, (dimethylsilyl-bis-methylcyclopentadienyl) hafnium 2-dimethylaminomethylphenyl, (dimethylsilyl-bis-ethylcyclopentadienyl) hafnium 2-dimethylaminobenzyl, (dimethylsilyl-bis-ethylcyclopentadienyl) hafnium -dimethylaminomethylphenyl, (dimethylsilyl-bis-t-butylcyclopentadienyl) hafnium 2-dimethylaminobenzyl, (dimethylsilyl-bis-n-butylcyclopentadienyl) hafnium 2-dimethylaminomethylphenyl, (dimethylsilyl-bis-t-butylcyclopentadienyl) hafnium 2-dimethylaminomethylphenyl, (dimethylsilyl-bis-tetramethylcyclopentadienyl) hafnium 2-dimethylaminobenzyl, (dimethylsilyl-bis-tetramethylcyclopentadienyl) hafnium 2-dimethylaminomethylphenyl, (dimethylsilyl-bis-indenyl) hafnium 2-dimethylaminobenzyl, (dimethylsilyl-bis-indenyl) hafnium 2-dimethylaminomethylphenyl, (dimethylsilyl-bis-tetrahydroindenyl) hafnium 2-dimethylaminobenzyl, (dimethylsilylbis-tetrahydroindenyl) hafnium 2-dimethylaminomethylphenyl, (dimethylsilyl-bis-fluorenyl) hafnium 2-dimethylaminobenzyl, (dimethylsilyl-bis-fluorenyl) hafnium 2-dimethylaminomethylphenyl, (dimethylsilyl-bis-tetrahydrofluorenyl) hafnium 2-dimethylaminobenzyl, (dimethylsilyl-bis-tetrahydrofluorenyl) hafnium 2-dimethylaminomethylphenyl, (dimethylsilyl-cyclopentadienyl-fluorenyl) hafnium 2-dimethylaminobenzyl, (dimethylsilyl-cyclopentadienyl-fluorenyl) hafnium 2-dimethylaminomethylphenyl, (isopropylidenecyclopentadienyl-fluorenyl) hafnium 2-dimethylaminobenzyl, and (isopropylidenecyclopentadienyl-fluorenyl) hafnium 2-dimethylaminomethylphenyl, [2,2'-biphenyldiylbis(3,4-dimethyl-1-cyclopentadienyl)]titanium 2-dimethylaminobenzyl, [6,6'-dimethyl-2,2'biphenylbis(3,4-dimethyl-1-cyclopentadienyl)]titanium 2-dimethylamino benzyl.

Exemplary complexes of formula $A_2$ include cyclopentadienyl titanium allyl chloride, methylcyclopentadienyl titanium allyl chloride, ethylcyclopentadienyl titanium allyl chloride, t-butylcyclopentadienyl titanium allyl chloride, n-butylcyclopentadienyl titanium allyl chloride, pentamethylcyclopentadienyl titanium allyl chloride, cyclopentadienyl titanium allyl bromide, methylcyclopentadienyl titanium allyl bromide, ethylcyclopentadienyl titanium allyl bromide, t-butylcyclopentadienyl titanium allyl bromide, n-butylcyclopentadienyl titanium allyl bromide, pentamethylcyclopentadienyl titanium allyl bromide, cyclopentadienyl titanium allyl methoxide, methylcyclopentadienyl titanium allyl methoxide, ethylcyclopentadienyl titanium allyl methoxide, t-butylcyclopentadienyl titanium allyl methoxide, n-butylcyclopentadienyltitanium allyl methoxide, pentamethylcyclopentadienyl titanium allyl methoxide, cyclopentadienyl titanium allyl ethoxide, methylcyclopentadienyl titanium allyl ethoxide, ethylcyclopentadienyl titanium allyl ethoxide, t-butylcyclopentadienyl titanium allyl ethoxide, n-butylcyclopentadienyl titanium allyl ethoxide, pentamethylcyclopentadienyl titanium allyl ethoxide, cyclopentadienyl titanium allyl isopropoxide, methylcyclopentadienyl titanium allyl isopropoxide, ethylcyclopentadienyl titanium allyl isopropoxide, t-butylcyclopentadienyl titanium allyl isopropoxide, n-butylcyclopentadienyl titanium allyl isopropoxide, pentamethylcyclopentadienyl titanium allyl isopropoxide, cyclopentadienyl titanium allyl phenoxide, methylcyclopentadienyl titanium allyl phenoxide, ethylcyclopentadienyl titanium allyl phenoxide, t-butylcyclopentadienyl titanium allyl phenoxide, n-butylcyclopentadienyl titanium allyl phenoxide, pentamethylcyclopentadienyl titanium allyl phenoxide, cyclopentadienyl titanium (2-methylallyl) chloride, methylcyclopentadienyl titanium (2-methylallyl) chloride, ethylcyclopentadienyl titanium (2-methylallyl) chloride, t-butylcyclopentadienyl titanium (2-methylallyl) chloride, pentamethylcyclopentadienyl titanium (2-methylallyl) chloride, n-butylcyclopentadienyl titanium (2-methylallyl) chloride, pentamethylcyclopentadienyl titanium (2-methylallyl) chloride, cyclopentadienyl titanium (2-methylallyl) bromide, methylcyclopentadienyl titanium (2-methylallyl) bromide, ethylcyclopentadienyl titanium (2-methylallyl) bromide, t-butylcyclopentadienyl titanium (2-methylallyl) bromide, n-butylcyclopentadienyl titanium (2-methylallyl) bromide, pentamethylcyclopentadienyl titanium (2-methylallyl) bromide, cyclopentadienyl titanium (2-methylallyl) methoxide, methylcyclopentadienyl titanium (2-methylallyl) methoxide, ethylcyclopentadienyl titanium (2-methylallyl) methoxide, butylcyclopentadienyl titanium (2-methylallyl) methoxide, pentamethylcyclopentadienyl titanium (2-methylallyl) methoxide, cyclopentadienyl titanium (2-methylallyl) ethoxide, methylcyclopentadienyl titanium (2-methylallyl) ethoxide, ethylcyclopentadienyl titanium (2-methylallyl) ethoxide, t-butylcyclopentadienyl titanium (2-methylallyl) ethoxide, n-butylcyclopentadienyl titanium (2-methylallyl) ethoxide, pentamethylcyclopentadienyl)titanium (2-methylallyl) ethoxide, cyclopentadienyl titanium (2-methylallyl) isopropoxide, methylcyclopentadienyl titanium (2-methylallyl) isopropoxide, ethylcyclopentadienyl titanium (2-methylallyl) isopropoxide, t-butylcyclopentadienyl titanium (2-methylallyl) isopropoxide, n-butylcyclopentadienyl titanium (2-methylallyl) isopropoxide, pentamethylcyclopentadienyl titanium (2-methylallyl) isopropoxide, cyclopentadienyl titanium (2-methylallyl) phenoxide, methylcyclopentadienyl titanium (2-methylallyl) phenoxide, ethylcyclopentadienyl titanium (2-methylallyl) phenoxide, t-butylcyclopentadienyl titanium (2-methylallyl) phenoxide, n-butylcyclopentadienyl titanium (2-methylallyl) phenoxide, pentamethylcyclopentadienyl titanium (2-methylallyl) phenoxide, cyclopentadienyl titanium (2-dimethylaminobenzyl) chloride, methylcyclopentadienyl titanium (2-dimethylaminobenzyl) chloride, ethylcyclopentadienyl titanium (2-dimethylaminobenzyl) chloride, t-butylcyclopentadienyl titanium (2-dimethylaminobenzyl) chloride, n-butylcyclopentadienyl titanium (2-dimethylaminobenzyl) chloride, pentamethylcyclopentadienyl titanium (2-dimethylaminobenzyl) chloride, cyclopentadienyl titanium (2-dimethylaminobenzyl) bromide, methylcyclopentadienyl titanium (2-dimethylaminobenzyl) bromide, ethylcyclopentadienyl titanium (2-dimethylaminobenzyl) bromide, t-butylcyclopentadienyl titanium (2-dimethylaminobenzyl) bromide, n-butylcyclopentadienyl titanium (2-dimethylaminobenzyl) bromide, pentamethylcyclopentadienyl titanium (2-dimethylaminobenzyl) bromide, cyclopentadienyl titanium (2-dimethylaminobenzyl) methoxide, methylcyclopentadienyl titanium (2-dimethylaminobenzyl) methoxide, ethylcyclopentadienyl titanium (2-dimethylaminobenzyl) methoxide, t-butylcyclopentadienyl titanium (2-dimethylaminobenzyl) methoxide, t-butylcyclopentadienyl titanium (2-dimethylaminobenzyl) methoxide, pentamethylcyclopentadienyl titanium (2-dimethylaminobenzyl) methoxide, cyclopentadienyl titanium (2-dimethylaminobenzyl) ethoxide, methylcyclopentadienyl titanium (2-dimethylaminobenzyl) ethoxide, ethylcyclopentadienyl titanium (2-dimethylaminobenzyl) ethoxide, t-butylcyclopentadienyl titanium (2-dimethylaminobenzyl) ethoxide, n-butylcyclopentadienyl titanium (2-dimethylaminobenzyl) ethoxide, pentamethylcyclopentadienyl titanium (2-dimethylaminobenzyl) ethoxide, cyclopentadienyl titanium (2-dimethylaminobenzyl) isopropoxide, methylcyclopentadienyl titanium (2-dimethylaminobenzyl) isopropoxide, ethylcyclopentadienyl titanium (2-dimethylaminobenzyl) isopropoxide, n-butylcyclopentadienyl titanium (2-dimethylaminobenzyl) isopropoxide, t-butylcyclopentadienyl titanium (2-dimethylaminobenzyl) isopropoxide, pentamethylcyclopentadienyl titanium (2-dimethylaminobenzyl) isopropoxide, cyclopentadienyl titanium (2-dimethylaminobenzyl) phenoxide, methylcyclopentadienyl titanium (2-dimethylaminobenzyl) phenoxide, ethylcyclopentadienyl titanium (2-di-methylaminobenzyl) phenoxide, butylcyclopentadienyl titanium (2-dimethylaminobenzyl) phenoxide, pentamethylcyclopentadienyl titanium (2-dimethylaminobenzyl) phenoxide, cyclopentadienyl titanium (2-dimethylaminomethylphenyl) chloride, methylcyclopentadienyl titanium (2-dimethylaminomethylphenyl) chloride, ethylcyclopentadienyl titanium (2-dimethylaminomethylphenyl) chloride, t-butylcyclopentadienyl titanium (2-dimethylaminomethylphenyl) chloride, n-butylcyclopentadienyl titanium (2-dimethylaminomethylphenyl) chloride, pentamethylcyclopentadienyl titanium (2-dimethylaminomethylphenyl) chloride, cyclopentadienyl titanium (2-dimethylaminomethylphenyl) bromide, methylcyclopentadienyl titanium (2-dimethylaminomethylphenyl) bromide, ethylcyclopentadienyl titanium (2-dimethylaminomethylphenyl) bromide, t-butylcyclopentadienyl titanium dimethylaminomethylphenyl) bromide, n-butylcyclopentadienyl titanium (2-dimethylaminomethylphenyl) bromide, pentamethylcyclopentadienyl titanium (2-dimethylaminomethylphenyl) bromide, cyclopentadienyl titanium (2-dimethylaminomethylphenyl) methoxide, methylcyclopentadienyl titanium (2-dimethylaminomethylphenyl) methoxide, ethylcyclopentadienyl titanium (2-dimethylaminomethylphenyl) methoxide, n-butylcyclopentadienyl titanium (2-dimethylaminomethylphenyl) methoxide, t-butylcyclopentadienyl titanium (2-dimethylaminomethylphenyl) methoxide, pentamethylcyclopentadienyl titanium (2-dimethylaminomethylphenyl) methoxide, cyclopentadienyl titanium (2-dimethylaminomethylphenyl) ethoxide, methylcyclopentadienyl titanium (2-dimethylaminomethylphenyl) ethoxide, ethylcyclopentadienyl titanium (2-dimethylaminomethylphenyl) ethoxide, n-butylcyclopentadienyl titanium (2-dimethylaminomethylphenyl) ethoxide, t-butylcyclopentadienyl titanium (2-dimethylaminomethylphenyl) ethoxide, pentamethylcyclopentadienyl titanium (2-dimethylaminomethylphenyl) ethoxide, cyclopentadienyl titanium (2-dimethylaminomethylphenyl) isopropoxide, methylcyclopentadienyl titanium (2-diethylaminomethylphenyl) isopropoxide, ethylcyclopentadienyl titanium (2-dimethylaminomethylphenyl) isopropoxide, n-butylcyclopentadienyl titanium (2-dimethylaminomethylphenyl) isopropoxide, t-butylcyclopentadienyl titanium (2-dimethylaminomethylphenyl) isopropoxide, pentamethylcyclopentadienyl titanium (2-dimethylaminomethylphenyl) isopropoxide, cyclopentadienyl titanium (2-dimethylaminomethylphenyl) phenoxide, methylcyclopentadienyl titanium (2-dimethylaminomethylphenyl) phenoxide, ethylcyclopentadienyl titanium (2-dimethylaminomethylphenyl) phenoxide, n-butylcyclopentadienyl titanium(2-dimethylaminomethylphenyl) phenoxide, t-butylcyclopentadienyl titanium(2-dimethylaminomethylphenyl) phenoxide, pentamethylcyclopentadienyl titanium (2-dimethylaminomethylphenyl) phenoxide, cyclopentadienyl titanium allyl dimethylamide, methylcyclopentadienyl titanium allyl dimethylamide, ethylcyclopentadienyl titanium allyldimethylamide, butylcyclopentadienyl titanium allyl dimethylamide, pentamethylcyclopentadienyl titanium allyl dimethylamide, cyclopentadienyl titanium allyl diethylamide, methylcyclopentadienyl titanium allyl diethylamide, ethylcyclopentadienyl titanium allyl diethylamide, n-butylcyclopentadienyl titanium allyl diethylamide, t-butylcyclopentadienyl titanium allyl diethylamide, pentamethylcyclopentadienyl titanium allyl diethylamide, cyclopentadienyl titanium allyl (di-t-butylamide), methylcyclopentadienyl titanium allyl (di-t-butylamine), ethylcyclopentadienyl titanium allyl (di-t-butylamide), butylcyclopentadienyl titanium allyl (di-t-butylamide), pentamethylcyclopentadienyl titanium allyl (di-t-butylamide), cyclopentadienyl titanium diallyl, cyclopentadienyl titanium (2-methylallyl) dimethylamide, methylcyclopentadienyl titanium (2-methylallyl) dimethylamide, ethylcyclopentadienyl titanium (2-methylallyl) dimethylamide, butylcyclopentadienyl titanium (2-methylallyl) dimethylamide, pentamethylcyclopentadienyl titanium (2-methylallyl) dimethylamide, cyclopentadienyl titanium (2-methylallyl) diethylamide, methylcyclopentadienyl titanium (2-methylallyl) diethylamide, ethylcyclopentadienyl titanium (2-methylallyl) diethylamide, butylcyclopentadienyl titanium (2-methylallyl) diethylamide, pentamethylcyclopentadienyl titanium (2-methylallyl) diethylamide, cyclopentadienyl titanium (2-methylallyl) (di-t-butylamide), methylcyclopentadienyl titanium (2-methylallyl) (di-t-butylamide), ethylcyclopentadienyl titanium (2-methylallyl) methoxide, butylcyclopentadienyl titanium (2-methylallyl) (di-t-butylamide), pentamethylcyclopentadienyl titanium (2-methylallyl) (di-t-butylamide), cyclopentadienyl titanium bis-(2-methylallyl), cyclopentadienyl titanium (2-dimethylaminobenzyl) dimethylamide, methylcyclopentadienyl titanium (2-dimethylaminobenzyl) dimethylamide, ethylcyclopentadienyl titanium (2-dimethylaminobenzyl) dimethylamide, n-butylcyclopentadienyl titanium (2-dimethylaminobenzyl) dimethylamide, t-butylcyclopentadienyl titanium (2-dimethylaminobenzyl) dimethylamide, pentamethylcyclopentadienyl titanium (2-dimethylaminobenzyl) dimethylamide, cyclopentadienyl titanium (2-dimethylaminobenzyl) diethylamide, methylcyclopentadienyl titanium (2-dimethylaminobenzyl) diethylamide, ethylcyclopentadienyl titanium (2-dimethylaminobenzyl) diethylamide, butylcyclopentadienyl titanium (2-dimethylaminobenzyl) diethylamide, pentamethylcyclopentadienyl titanium (2-dimethylaminobenzyl) diethylamide, cyclopentadienyl titanium (2-dimethylaminobenzyl) methoxide, methylcyclopentadienyl titanium (2-dimethylaminobenzyl) (di-t-butylamide), ethylcyclopentadienyl titanium (2-dimethylaminobenzyl) (di-t-butylamide), butylcyclopentadienyl titanium (2-dimethylaminobenzyl) (di-t-butylamide), pentamethylcyclopentadienyl titanium (2-dimethylaminobenzyl) methoxide, cyclopentadienyl titanium bis-(2-dimethylaminobenzyl), cyclopentadienyl titanium (2-dimethylaminomethylphenyl) dimethylamide, methylcyclopentadienyl titanium (2-dimethylaminomethylphenyl) dimethylamide, ethylcyclopentadienyl titanium (2-dimethylaminomethylphenyl) dimethylamide, butylcyclopentadienyl titanium (2-dimethylaminomethylphenyl) dimethylamide, pentamethylcyclopentadienyl titanium (2-dimethylaminomethylphenyl) dimethylamide, cyclopentadienyl titanium (2-dimethylaminomethylphenyl) diethylamide, methylcyclopentadienyl titanium (2-dimethylaminomethylphenyl) diethylamide, ethylcyclopentadienyl titanium (2-dimethylaminomethylphenyl) diethylamide, butylcyclopentadienyl titanium (2-dimethylaminomethylphenyl) diethylamide, pentamethylcyclopentadienyl titanium (2-dimethylaminomethylphenyl) diethylamide, cyclopentadienyl titanium (2-dimethylaminomethylphenyl) (di-t-butylamide), methylcyclopentadienyl titanium (2-dimethylaminomethylphenyl) (di-t-butylamide), ethylcyclopentadienyl titanium (2-dimethylaminomethylphenyl) (di-t-butylamide), butylcyclopentadienyl titanium (2-dimethylaminomethylphenyl) (di-t-butylamide), pentamethylcyclopentadienyl titanium (2-dimethylaminomethylphenyl) (di-t-butylamide), cyclopentadienyl titanium bis-(2-di-methylaminomethylphenyl), cyclopentadienyl titanium methyl 2-dimethylaminobenzyl, cyclopentadienyl titanium benzyl 2-dimethylaminobenzyl, cyclopentadienyl titanium trimethylsilylmethyl 2-(dimethylamino)benzyl, methylcyclopentadienyl titanium methyl 2-dimethylaminobenzyl, methylcyclopentadienyl titanium benzyl 2-dimethylaminobenzyl, methylcyclopentadienyl titanium trimethylsilylmethyl 2-(dimethylamino)benzyl, pentamethylcyclopentadienyl titanium methyl 2-dimethylaminobenzyl, pentamethylcyclopentadienyl titanium benzyl 2-dimethylaminobenzyl, pentamethylcyclopentadienyl titanium trimethylsilylmethyl 2-(dimethylamino)benzyl, cyclopentadienyl zirconium allyl chloride, methylcyclopentadienyl zirconium allyl chloride, ethylcyclopentadienyl zirconium allyl chloride, t-butylcyclopentadienyl zirconium allyl chloride, pentamethylcyclopentadienyl zirconium allyl chloride, cyclopentadienyl zirconium allyl bromide, methylcyclopentadienyl zirconium allyl bromide, ethylcyclopentadienyl zirconium allyl bromide, n-butylcyclopentadienyl zirconium allyl bromide, t-butylcyclopentadienyl zirconium allyl bromide, pentamethylcyclopentadienyl zirconium allyl bromide, cyclopentadienyl zirconium allyl methoxide, methylcyclopentadienyl zirconium allyl methoxide, ethylcyclopentadienyl zirconium allyl methoxide, n-butylcyclopentadienyl zirconium allyl methoxide, t-butylcyclopentadienyl zirconium allyl methoxide, pentamethylcyclopentadienyl zirconium allyl methoxide, cyclopentadienyl zirconium allyl ethoxide, methylcyclopentadienyl zirconium allyl ethoxide, ethylcyclopentadienyl zirconium allyl ethoxide, n-butylcyclopentadienyl zirconium allyl ethoxide, t-butylcyclopentadienyl zirconium allyl ethoxide, pentamethylcyclopentadienyl zirconium allyl ethoxide, cyclopentadienyl zirconium allyl isopropoxide, methylcyclopentadienyl zirconium allyl isopropoxide, ethylcyclopentadienyl zirconium allyl isopropoxide, n-butylcyclopentadienyl zirconium allyl isopropoxide, t-butylcyclopentadienyl zirconium allyl isopropoxide, pentamethylcyclopentadienyl zirconium allyl isopropoxide, cyclopentadienyl zirconium allyl phenoxide, methylcyclopentadienyl zirconium allyl phenoxide, ethylcyclopentadienyl zirconium allyl phenoxide, n-butylcyclopentadienyl zirconium allyl phenoxide, t-butylcyclopentadienyl zirconium allyl phenoxide, pentamethylcyclopentadienyl zirconium allyl phenoxide, cyclopentadienyl zirconium (2-methylallyl) chloride, methylcyclopentadienyl zirconium (2-methylallyl) chloride, ethylcyclopentadienyl zirconium (2-methylallyl) chloride, n-butylcyclopentadienyl zirconium (2-methylallyl) chloride, t-butylcyclopentadienyl zirconium (2-methylallyl) chloride, pentamethylcyclopentadienyl zirconium (2-methylallyl) chloride, cyclopentadienyl zirconium (2-methylallyl) bromide, methylcyclopentadienyl zirconium (2-methylallyl) bromide, ethylcyclopentadienyl zirconium (2-methylallyl) bromide, n-butylcyclopentadienyl zirconium (2-methylallyl) bromide, t-butylcyclopentadienyl zirconium (2-methylallyl) bromide, pentamethylcyclopentadienyl zirconium (2-methylallyl) bromide, cyclopentadienyl zirconium (2-methylallyl) methoxide, methylcyclopentadienyl zirconium (2-methylallyl) methoxide, ethylcyclopentadienyl zirconium (2-methylallyl) methoxide, butylcyclopentadienyl zirconium (2-methylallyl) methoxide, pentamethylcyclopentadienyl zirconium (2-methylallyl) methoxide, cyclopentadienyl zirconium (2-methylallyl) ethoxide, methylcyclopentadienyl zirconium (2-methylallyl) ethoxide, ethylcyclopentadienyl zirconium (2-methylallyl) ethoxide, butylcyclopentadienyl zirconium (2-methylallyl) ethoxide, pentamethylcyclopentadienyl zirconium (2-methylallyl) ethoxide, cyclopentadienyl zirconium (2-methylallyl) isopropoxide, methylcyclopentadienyl zirconium (2-methylallyl) isopropoxide, ethylcyclopentadienyl zirconium (2-methylallyl) isopropoxide, n-butylcyclopentadienyl zirconium (2-methylallyl) isopropoxide, t-butylcyclopentadienyl zirconium (2-methylallyl) isopropoxide, pentamethylcyclopentadienyl zirconium (2-methylallyl) isopropoxide, cyclopentadienyl zirconium (2-methylallyl) phenoxide, methylcyclopentadienyl zirconium (2-methylallyl) phenoxide, ethylcyclopentadienyl zirconium (2-methylallyl) phenoxide, n-butylcyclopentadienyl zirconium (2-methylallyl) phenoxide, t-butylcyclopentadienyl zirconium (2-methylallyl) phenoxide, pentamethylcyclopentadienyl zirconium (2-methylallyl) phenoxide, cyclopentadienyl zirconium (2-dimethylaminobenzyl) chloride, methylcyclopentadienyl zirconium (2-dimethylaminobenzyl) chloride, ethylcyclopentadienyl zirconium (2-dimethylaminobenzyl) chloride, n-butylcyclopentadienyl zirconium (2-dimethylaminobenzyl) chloride, t-butylcyclopentadienyl zirconium (2-dimethylaminobenzyl) chloride, pentamethylcyclopentadienyl zirconium (2-dimethylaminobenzyl) chloride cyclopentadienyl zirconium (2-dimethylaminobenzyl bromide, methylcyclopentadienyl zirconium (2-dimethylaminobenzyl) bromide, ethylcyclopentadienyl zirconium (2-dimethylaminobenzyl) bromide, n-butylcyclopentadienyl zirconium (2-dimethylaminobenzyl bromide, t-butylcyclopentadienyl zirconium (2-dimethylaminobenzyl) bromide, pentamethylcyclopentadienyl zirconium (2-dimethylaminobenzyl) bromide, cyclopentadienyl zirconium (2-dimethylaminobenzyl) methoxide, methylcyclopentadienyl zirconium (2-dimethylaminobenzyl) methoxide, ethylcyclopentadienyl zirconium (2-dimethylaminobenzyl) methoxide, butylcyclopentadienyl zirconium (2-dimethylaminobenzyl) methoxide, pentamethylcyclopentadienyl zirconium (2-dimethylaminobenzyl) methoxide, cyclopentadienyl zirconium (2-dimethylaminobenzyl) ethoxide, methylcyclopentadienyl zirconium (2-dimethylaminobenzyl) ethoxide, ethylcyclopentadienyl zirconium (2-dimethylaminobenzyl) ethoxide, butylcyclopentadienyl zirconium (2-dimethylaminobenzyl) ethoxide, pentamethylcyclopentadienyl zirconium (2-dimethylaminobenzyl) ethoxide, cyclopentadienyl zirconium (2-dimethylaminobenzyl) isopropoxide, methylcyclopentadienyl zirconium (2-dimethylaminobenzyl) isopropoxide, ethylcyclopentadienyl zirconium (2-dimethylaminobenzyl) isopropoxide, butylcyclopentadienyl zirconium (2-dimethylaminobenzyl) isopropoxide, pentamethylcyclopentadienyl zirconium (2-dimethylaminobenzyl) isopropoxide, cyclopentadienyl zirconium (2-dimethylaminobenzyl) phenoxide, methylcyclopentadienyl zirconium (2-dimethylaminobenzyl) phenoxide, ethylcyclopentadienyl zirconium (2-dimethylaminobenzyl) phenoxide, butylcyclopentadienyl zirconium (2-dimethylaminobenzyl) phenoxide, pentamethylcyclopentadienyl zirconium (2-dimethylaminobenzyl) phenoxide, cyclopentadienyl zirconium (2-dimethylaminomethylphenyl) chloride, methylcyclopentadienyl zirconium (2-dimethylaminomethylphenyl) chloride, ethylcyclopentadienyl zirconium (2-dimethylaminomethylphenyl) chloride, butylcyclopentadienyl zirconium (2-dimethylaminomethylphenyl) chloride, pentamethylcyclopentadienyl zirconium (2-dimethylaminomethylphenyl) chloride, cyclopentadienyl zirconium (2-dimethylaminomethylphenyl) bromide, methylcyclopentadienyl zirconium (2-dimethylaminomethylphenyl) bromide, ethylcyclopentadienyl zirconium (2-dimethylaminomethylphenyl) bromide, butylcyclopentadienyl zirconium (2-dimethylaminomethylphenyl) bromide, pentamethylcyclopentadienyl zirconium (2-dimethylaminomethylphenyl) bromide, cyclopentadienyl zirconium (2-dimethylaminomethylphenyl) methoxide, methylcyclopentadienyl zirconium (2-dimethylaminomethylphenyl) methoxide, ethylcyclopentadienyl zirconium (2-dimethylaminomethylphenyl) methoxide, butylcyclopentadienyl zirconium (2-dimethylaminomethylphenyl) methoxide, pentamethylcyclopentadienyl zirconium (2-dimethylaminomethylphenyl) methoxide, cyclopentadienyl zirconium (2-dimethylaminomethylphenyl) ethoxide, methylcyclopentadienyl zirconium (2-dimethylaminomethylphenyl) ethoxide, ethylcyclopentadienyl zirconium (2-dimethylaminomethylphenyl) ethoxide, t-butylcyclopentadienyl zirconium (2-dimethylaminomethylphenyl) ethoxide, n-butylcyclopentadienyl zirconium (2-dimethylaminomethylphenyl) ethoxide, pentamethylcyclopentadienyl zirconium (2-dimethylaminomethylphenyl) ethoxide, cyclopentadienyl zirconium (2-dimethylaminomethylphenyl) isopropoxide, methylcyclopentadienyl zirconium (2-dimethylaminomethylphenyl) isopropoxide, ethylcyclopentadienyl zirconium (2-dimethylaminomethylphenyl) isopropoxide, n-butylcyclopentadienyl (2-dimethylaminomethylphenyl) isopropoxide, t-butylcyclopentadienyl zirconium (2-dimethylaminomethylphenyl) isopropoxide, pentamethylcyclopentadienyl zirconium (2-diethylaminomethylphenyl) isopropoxide, cyclopentadienyl zirconium (2-dimethylaminomethylphenyl) phenoxide, methylcyclopentadienyl zirconium (2-dimethylaminomethylphenyl) phenoxide, ethylcyclopentadienyl zirconium (2-dimethylaminomethylphenyl) phenoxide, n-butylcyclopentadienyl zirconium (2-dimethylaminomethylphenyl) phenoxide, t-butylcyclopentadienyl zirconium (2-dimethylaminomethylphenyl) phenoxide, pentamethylcyclopentadienyl zirconium (2-dimethylaminomethylphenyl) phenoxide, cyclopentadienyl zirconium allyl dimethylamide, methylcyclopentadienyl zirconium allyl dimethylamide, ethylcyclopentadienyl zirconium allyl dimethylamide, n-butylcyclopentadienyl zirconium allyl dimethylamide, t-butylcyclopentadienyl zirconium allyl dimethylamide, pentamethylcyclopentadienyl zirconium allyl dimethylamide, cyclopentadienyl zirconium allyl diethylamide, methylcyclopentadienyl zirconium allyl diethylamide, ethylcyclopentadienyl zirconium allyl diethylamide, n-butylcyclopentadienyl zirconium allyl diethylamide, t-butylcyclopentadienyl zirconium allyl diethylamide, pentamethylcyclopentadienyl zirconium allyl diethylamide, cyclopentadienyl zirconium allyl (di-t-butylamide), methylcyclopentadienyl zirconium allyl (di-t-butylamide), ethylcyclopentadienyl zirconium allyl (di-t-butylamide), n-butylcyclopentadienyl zirconium allyl (di-t-butylamide), t-butylcyclopentadienyl zirconium allyl (di-t-butylamide), pentamethylcyclopentadienyl zirconium allyl (di-t-butylamide), cyclopentadienyl zirconium diallyl, cyclopentadienyl zirconium (2-methylallyl) dimethylamide, methylcyclopentadienyl zirconium (2-methylallyl) dimethylamide, ethylcyclopentadienyl zirconium (2-methylallyl) dimethylamide, n-butylcyclopentadienyl zirconium (2-methylallyl) dimethylamide, t-butylcyclopentadienyl zirconium (2-methylallyl) dimethylamide, pentamethylcyclopentadienyl zirconium (2-methylallyl) dimethylamide, cyclopentadienyl zirconium (2-methylallyl) diethylamide, methylcyclopentadienyl zirconium (2-methylallyl) diethylamide, ethylcyclopentadienyl zirconium (2-methylallyl) diethylamide, butylcyclopentadienyl zirconium (2-methylallyl) diethylamide, pentamethylcyclopentadienyl zirconium (2-methylallyl) diethylamide, cyclopentadienyl zirconium (2-methylallyl) (di-t-butylamide), methylcyclopentadienyl zirconium (2-methylallyl) (di-t-butylamide), methylcyclopentadienyl zirconium (2-methylallyl) methoxide, butylcyclopentadienyl zirconium (2-methylallyl) (di-t-butylamide), pentamethylcyclopentadienyl zirconium (2-methylallyl) (di-t-butylamide), cyclopentadienyl zirconium bis-(2-methylallyl), cyclopentadienyl zirconium (2-dimethylaminobenzyl) dimethylamide, methylcyclopentadienyl zirconium (2-dimethylaminobenzyl) dimethylamide, ethylcyclopentadienyl zirconium (2-dimethylaminobenzyl) dimethylamide, n-butylcyclopentadienyl zirconium (2-dimethylaminobenzyl) dimethylamide, t-butylcyclopentadienyl zirconium (2-dimethylaminobenzyl) dimethylamide, pentamethylcyclopentadienyl zirconium (2-dimethylaminobenzyl) dimethylamide, cyclopentadienyl zirconium (2-dimethylaminobenzyl) diethylamide, methylcyclopentadienyl zirconium (2-dimethylaminobenzyl) diethylamide, ethylcyclopentadienyl zirconium (2-dimethylaminobenzyl) diethylamide, n-butylcyclopentadienyl zirconium (2-dimethylaminobenzyl) diethylamide, t-butylcyclopentadienyl zirconium (2-dimethylaminobenzyl) diethylamide, pentamethylcyclopentadienyl zirconium (2-dimethylaminobenzyl) diethylamide, cyclopentadienyl zirconium (2-dimethylaminobenzyl) methoxide, methylcyclopentadienyl zirconium (2-dimethylaminobenzyl) (di-t-butylamide), ethylcyclopentadienyl zirconium (2-dimethylaminobenzyl) (di-t-butylamide), n-butylcyclopentadienyl zirconium (2-dimethylaminobenzyl) (di-t-butylamide), t-butylcyclopentadienyl zirconium (2-dimethylaminobenzyl) (di-t-butylamide), pentamethylcyclopentadienyl zirconium (2-dimethylaminobenzyl) methoxide, cyclopentadienyl zirconium bis-(2-dimethylaminobenzyl), cyclopentadienyl zirconium (2-dimethylaminomethylphenyl) dimethylamide, methylcyclopentadienyl zirconium (2-dimethylaminomethylphenyl) dimethylamide, ethylcyclopentadienyl zirconium (2-dimethylaminomethylphenyl) dimethylamide, butylcyclopentadienyl zirconium (2-dimethylaminomethylphenyl) dimethylamide, pentamethylcyclopentadienyl zirconium (2-dimethylaminomethylphenyl) dimethylamide, cyclopentadienyl zirconium (2-diethylaminomethylphenyl) diethylamide, methylcyclopentadienyl zirconium (2-dimethylaminomethylphenyl) diethylamide, ethylcyclopentadienyl zirconium (2-dimethylaminomethylphenyl) diethylamide, n-butylcyclopentadienyl zirconium (2-dimethylaminomethylphenyl) diethylamide, t-butylcyclopentadienyl zirconium (2-dimethylaminomethylphenyl) diethylamide, pentamethylcyclopentadienyl zirconium (2-dimethylaminomethylphenyl) diethylamide, cyclopentadienyl zirconium (2-dimethylaminomethylphenyl) (di-t-butylamide), methylcyclopentadienyl zirconium (2-dimethylaminomethylphenyl) (di-t-butylamide), ethylcyclopentadienyl zirconium (2-dimethylaminomethylphenyl) (di-t-butylamide), n-butylcyclopentadienyl zirconium (2-dimethylaminomethylphenyl) (di-t-butylamide), t-butylcyclopentadienyl zirconium (2-dimethylaminomethylphenyl) (di-t-butylamide), pentamethylcyclopentadienyl zirconium (2-dimethylaminomethylphenyl) (di-t-butylamide), cyclopentadienyl zirconium bis-(2-dimethylaminomethylphenyl), cyclopentadienyl zirconium methyl 2-dimethylaminobenzyl, cyclopentadienyl zirconium benzyl 2-dimethylaminobenzyl, cyclopentadienyl zirconium trimethylsilylmethyl 2-(di-methylamino)benzyl, methylcyclopentadienyl zirconium methyl 2-dimethylaminobenzyl, methylcyclopentadienyl zirconium benzyl 2-dimethylaminobenzyl, methylcyclopentadienyl zirconium trimethylsilylmethyl 2-(dimethylamino)benzyl, pentamethylcyclopentadienyl zirconium methyl 2-dimethylaminobenzyl, pentamethylcyclopentadienyl zirconium benzyl 2-dimethylaminobenzyl, pentamethylcyclopentadienyl zirconium trimethylsilylmethyl 2-(dimethylamino)benzyl, cyclopentadienyl hafnium allyl chloride, methylcyclopentadienyl hafnium allyl chloride, ethylcyclopentadienyl hafnium allyl chloride, n-butylcyclopentadienyl hafnium allyl chloride, t-butylcyclopentadienyl hafnium allyl chloride, pentamethylcyclopentadienyl hafnium allyl chloride, cyclopentadienyl hafnium allyl bromide, methylcyclopentadienyl hafnium allyl bromide, ethylcyclopentadienyl hafnium allyl bromide, n-butylcyclopentadienyl hafnium allyl bromide, t-butylcyclopentadienyl hafnium allyl bromide, pentamethylcyclopentadienyl hafnium allyl bromide, cyclopentadienyl hafnium allyl methoxide, methylcyclopentadienyl hafnium allyl methoxide, ethylcyclopentadienyl hafnium allyl methoxide, n-butylcyclopentadienyl hafnium allyl methoxide, t-butylcyclopentadienyl hafnium allyl methoxide, pentamethylcyclopentadienyl hafnium allyl methoxide, cyclopentadienyl hafnium allyl ethoxide, methylcyclopentadienyl hafnium allyl ethoxide, ethylcyclopentadienyl hafnium allyl ethoxide, n-butylcyclopentadienyl hafnium allyl ethoxide, t-butylcyclopentadienyl hafnium allyl ethoxide, pentamethylcyclopentadienyl hafnium allyl ethoxide, cyclopentadienyl hafnium allyl isopropoxide, methylcyclopentadienyl hafnium allyl isopropoxide, ethylcyclopentadienyl hafnium allyl isopropoxide, n-butylcyclopentadienyl hafnium allyl isopropoxide, t-butylcyclopentadienyl hafnium allyl isopropoxide, pentamethylcyclopentadienyl hafnium allyl isopropoxide, cyclopentadienyl hafnium allyl phenoxide, methylcyclopentadienyl hafnium allyl phenoxide, ethylcyclopentadienyl hafnium allyl phenoxide, n-butylcyclopentadienyl hafnium allyl phenoxide, t-butylcyclopentadienyl hafnium allyl phenoxide, pentamethylcyclopentadienyl hafnium allyl phenoxide, cyclopentadienyl hafnium (2-methylallyl) chloride, methylcyclopentadienyl hafnium (2-methylallyl) chloride, ethylcyclopentadienyl hafnium (2-methylallyl) chloride, n-butylcyclopentadienyl hafnium (2-methylallyl) chloride, t-butylcyclopentadienyl hafnium (2-methylallyl) chloride, pentamethylcyclopentadienyl hafnium (2-methylallyl) chloride, cyclopentadienyl hafnium (2-methylallyl) bromide, methylcyclopentadienyl hafnium (2-methylallyl) bromide, ethylcyclopentadienyl hafnium (2-methylallyl) bromide, n-butylcyclopentadienyl hafnium (2-methylallyl) bromide, t-butylcyclopentadienyl hafnium (2-methylallyl) bromide, pentamethylcyclopentadienyl hafnium (2-methylallyl) bromide, cyclopentadienyl hafnium (2-methylallyl) methoxide, methylcyclopentadienyl hafnium (2-methylallyl) methoxide, ethylcyclopentadienyl hafnium (2-methylallyl) methoxide, n-butylcyclopentadienyl hafnium (2-methylallyl) methoxide, t-butylcyclopentadienyl hafnium (2-methylallyl) methoxide, pentamethylcyclopentadienyl hafnium (2-methylallyl) methoxide, cyclopentadienyl hafnium (2-methylallyl)ethoxide, methylcyclopentadienyl hafnium (2-methylallyl) ethoxide, ethylcyclopentadienyl hafnium (2-methylallyl) ethoxide, t-butyl-cyclopentadienyl hafnium (2-methylallyl) ethoxide, t-butylcyclopentadienyl hafnium (2-methylallyl) ethoxide, pentamethylcyclopentadienyl hafnium (2-methylallyl) ethoxide, cyclopentadienyl hafnium (2-methylallyl) isopropoxide, methylcyclopentadienyl hafnium (2-methylallyl) isopropoxide, ethylcyclopentadienyl hafnium (2-methylallyl) isopropoxide, n-butylcyclopentadienyl hafnium (2-methylallyl) isopropoxide, t-butylcyclopentadienyl hafnium (2-methylallyl) isopropoxide, pentamethylcyclopentadienyl hafnium (2-methylallyl) isopropoxide, cyclopentadienyl hafnium (2-methylallyl) phenoxide, methylcyclopentadienyl hafnium (2-methylallyl) phenoxide, ethylcyclopentadienyl hafnium (2-methylallyl) phenoxide, n-butylcyclopentadienyl hafnium (2-methylallyl) phenoxide, t-butylcyclopentadienyl hafnium (2-methylallyl) phenoxide, pentamethylcyclopentadienyl hafnium (2-methylallyl) phenoxide, cyclopentadienyl hafnium (2-dimethylaminobenzyl) chloride, methylcyclopentadienyl hafnium (2-dimethylaminobenzyl) chloride, ethylcyclopentadienyl hafnium (2-dimethylaminobenzyl) chloride, n-butylcyclopentadienyl hafnium (2-dimethylaminobenzyl) chloride, t-butylcyclopentadienyl hafnium (2-dimethylaminobenzyl) chloride, pentamethylcyclopentadienyl hafnium (2-dimethylaminobenzyl) chloride, cyclopentadienyl hafnium (2-dimethylaminobenzyl) bromide, methylcyclopentadienyl hafnium (2-dimethylaminobenzyl) bromide, ethylcyclopentadienyl hafnium (2-dimethylaminobenzyl) bromide, n-butylcyclopentadienyl hafnium (2-dimethylaminobenzyl) bromide, t-butylcyclopentadienyl hafnium (2-dimethylaminobenzyl) bromide, pentamethylcyclopentadienyl hafnium (2-dimethylaminobenzyl) bromide, cyclopentadienyl hafnium (2-dimethylaminobenzyl) methoxide, methylcyclopentadienyl hafnium (2-dimethylaminobenzyl) methoxide, ethylcyclopentadienyl hafnium (2-dimethylaminobenzyl) methoxide, t-butylcyclopentadienyl hafnium (2-dimethylaminobenzyl) methoxide, t-butylcyclopentadienyl hafnium (2-dimethylaminobenzyl) methoxide, pentamethylcyclopentadienyl hafnium (2-dimethylaminobenzyl) methoxide, cyclopentadienyl hafnium (2-dimethylaminobenzyl) ethoxide, methylcyclopentadienyl hafnium (2-dimethylaminobenzyl) ethoxide, ethylcyclopentadienyl hafnium (2-dimethylaminobenzyl) ethoxide, n-butylcyclopentadienyl hafnium (2-dimethylaminobenzyl) ethoxide, t-butylcyclopentadienyl hafnium (2-dimethylaminobenzyl) ethoxide, pentamethylcyclopentadienyl hafnium (2-dimethylaminobenzyl) ethoxide, cyclopentadienyl hafnium (2-dimethylaminobenzyl) isopropoxide, methylcyclopentadienyl hafnium (2-dimethylaminobenzyl) isopropoxide, ethylcyclopentadienyl hafnium (2-dimethylaminobenzyl) isopropoxide, n-butylcyclopentadienyl hafnium (2-dimethylaminobenzyl) isopropoxide, t-butylcyclopentadienyl hafnium (2-dimethylaminobenzyl) isopropoxide, pentamethylcyclopentadienyl hafnium (2-dimethylaminobenzyl) isopropoxide, cyclopentadienyl hafnium (2-dimethylaminobenzyl) phenoxide, methylcyclopentadienyl hafnium (2-dimethylaminobenzyl) phenoxide, ethylcyclopentadienyl hafnium (2-dimethylaminobenzyl) phenoxide, n-butylcyclopentadienyl hafnium (2-dimethylaminobenzyl) phenoxide, t-butylcyclopentadienyl hafnium (2-dimethylaminobenzyl) phenoxide, pentamethylcyclopentadienyl hafnium (2-dimethylaminobenzyl) phenoxide, cyclopentadienyl hafnium (2-dimethylaminomethylphenyl) chloride, methylcyclopentadienyl hafnium (2-dimethylaminomethylphenyl) chloride, ethylcyclopentadienyl hafnium (2-dimethylaminomethylphenyl) chloride, n-butylcyclopentadienyl hafnium (2-dimethylaminomethylphenyl) chloride, t-butylcyclopentadienyl hafnium (2-dimethylaminomethylphenyl) chloride, pentamethylcyclopentadienyl hafnium (2-dimethylaminomethylphenyl) chloride, cyclopentadienyl hafnium (2-dimethylaminomethylphenyl) bromide, methylcyclopentadienyl hafnium (2-dimethylaminomethylphenyl) bromide, ethylcyclopentadienyl hafnium (2-dimethylaminomethylphenyl) bromide, t-butylcyclopentadienyl hafnium (2-dimethylaminomethylphenyl) bromide, pentamethylcyclopentadienyl hafnium (2-dimethylaminomethylphenyl) bromide, cyclopentadienyl hafnium (2-dimethylaminomethylphenyl) methoxide, methylcyclopentadienyl hafnium (2-dimethylaminomethylphenyl) methoxide, ethylcyclopentadienyl hafnium (2-dimethylaminomethylphenyl) methoxide, n-butylcyclopentadienyl hafnium (2-dimethylaminomethylphenyl) methoxide, t-butylcyclopentadienyl hafnium (2-dimethylaminomethylphenyl) methoxide, pentamethylcyclopentadienyl hafnium (2-dimethylaminomethylphenyl) methoxide, cyclopentadienyl hafnium (2-dimethylaminomethylphenyl) ethoxide, methylcyclopentadienyl hafnium (2-dimethylaminomethylphenyl) ethoxide, ethylcyclopentadienyl hafnium (2-dimethylaminomethylphenyl) ethoxide, n-butylcyclopentadienyl hafnium (2-dimethylaminomethylphenyl) ethoxide, t-butylcyclopentadienyl hafnium (2-dimethylaminomethylphenyl) ethoxide, pentamethylcyclopentadienyl hafnium (2-dimethylaminomethylphenyl) ethoxide, cyclopentadienyl hafnium (2-dimethylaminomethylphenyl) isopropoxide, methylcyclopentadienyl hafnium (2-dimethylaminomethylphenyl) isopropoxide, ethylcyclopentadienyl hafnium (2-dimethylaminomethylphenyl) isopropoxide, n-butylcyclopentadienyl hafnium (2-dimethylaminomethylphenyl) isopropoxide, t-butylcyclopentadienyl hafnium (2-dimethylaminomethylphenyl) isopropoxide, pentamethylcyclopentadienyl hafnium (2-dimethylaminomethylphenyl) isopropoxide, cyclopentadienyl hafnium (2-dimethylaminomethylphenyl) phenoxide, methylcyclopentadienyl hafnium (2-dimethylaminomethylphenyl) phenoxide, ethylcyclopentadienyl hafnium (2-dimethylaminomethylphenyl) phenoxide, n-butylcyclopentadienyl hafnium (2-dimethylaminomethylphenyl phenoxide, t-butylcyclopentadienyl hafnium (2-dimethylaminomethylphenyl phenoxide, pentamethylcyclopentadienyl hafnium (2-dimethylaminomethylphenyl) phenoxide, cyclopentadienyl hafnium allyl dimethylamide, methylcyclopentadienyl hafnium allyl dimethylamide, ethylcyclopentadienyl hafnium allyl dimethylamide, t-butylcyclopentadienyl hafnium allyl dimethylamide, pentamethylcyclopentadienyl hafnium allyl dimethylamide, cyclopentadienyl hafnium allyl diethylamide, methylcyclopentadienyl hafnium allyl diethylamide, ethylcyclopentadienyl hafnium allyl diethylamide, butylcyclopentadienyl hafnium allyl diethylamide, pentamethylcyclopentadienyl hafnium allyl diethylamide, cyclopentadienyl hafnium allyl (di-t-butylamide), methylcyclopentadienyl hafnium allyl (di-t-butylamide), ethylcyclopentadienyl hafnium allyl (di-t-butylamide), butylcyclopentadienyl hafnium allyl (di-t-butylamide), pentamethylcyclopentadienyl hafnium allyl (di-t-butylamide), cyclopentadienyl hafnium diallyl, cyclopentadienyl hafnium (2-methylallyl) dimethylamide, methylcyclopentadienyl hafnium (2-methylallyl) dimethylamide, ethylcyclopentadienyl hafnium (2-methylallyl) dimethylamide, n-butylcyclopentadienyl hafnium (2-methylallyl) dimethylamide, t-butyl-cyclopentadienyl hafnium (2-methylallyl) dimethylamide, pentamethylcyclopentadienyl hafnium (2-methylallyl) dimethylamide, cyclopentadienyl hafnium (2-methylallyl) diethylamide, methylcyclopentadienyl hafnium (2-methylallyl) diethylamide, ethylcyclopentadienyl hafnium (2-methylallyl) diethylamide, n-butylcyclopentadienyl hafnium (2-methylallyl) diethylamide, t-butylcyclopentadienyl hafnium (2-methylallyl) diethylamide, pentamethylcyclopentadienyl hafnium (2-methylallyl) diethylamide, cyclopentadienyl hafnium (2-methylallyl) (di-t-butylamide), methylcyclopentadienyl hafnium (2-methylallyl) (di-t-butylamide), ethylcyclopentadienyl hafnium (2-methylallyl) methoxide, n-butylcyclopentadienyl hafnium (2-methylallyl) (di-t-butylamide), t-butylcyclopentadienyl hafnium (2-methylallyl) (di-t-butylamide), pentamethylcyclopentadienyl hafnium (2-methylallyl) (di-t-butylamide), cyclopentadienyl hafnium bis-(2-methylallyl), cyclopentadienyl hafnium (2-dimethylaminobenzyl) dimethylamide, methylcyclopentadienyl hafnium (2-dimethylaminobenzyl) dimethylamide, ethylcyclopentadienyl hafnium (2-dimethylaminobenzyl) dimethylamide, n-butylcyclopentadienyl hafnium (2-dimethylaminobenzyl) dimethylamide, t-butylcyclopentadienyl hafnium (2-dimethylaminobenzyl) dimethylamide, pentamethylcyclopentadienyl hafnium (2-dimethylaminobenzyl) dimethylamide, cyclopentadienyl hafnium (2-dimethylaminobenzyl) diethylamide, methylcyclopentadienyl hafnium (2-dimethylaminobenzyl) diethylamide, ethylcyclopentadienyl hafnium (2-dimethylaminobenzyl) diethylamide, n-butylcyclopentadienyl hafnium (2-dimethylaminobenzyl) diethylamide, t-butylcyclopentadienyl hafnium (2-di-methylaminobenzyl) diethylamide, pentamethylcyclopentadienyl hafnium (2-dimethylaminobenzyl) diethylamide, cyclopentadienyl hafnium (2-dimethylaminobenzyl) methoxide, methylcyclopentadienyl hafnium (2-dimethylaminobenzyl) (di-t-butylamide), ethylcyclopentadienyl hafnium (2-dimethylaminobenzyl) (di-t-butylamide), n-butylcyclopentadienyl hafnium (2-dimethylaminobenzyl) (di-t-butylamide), t-butylcyclopentadienyl hafnium (2-dimethylaminobenzyl) (di-t-butylamide), pentamethylcyclopentadienyl hafnium (2-dimethylaminobenzyl) methoxide, cyclopentadienyl hafnium bis-(2-dimethylaminobenzyl), cyclopentadienyl hafnium (2-dimethylaminomethylphenyl) dimethylamide, methylcyclopentadienyl hafnium (2-dimethylaminomethylphenyl) dimethylamide, ethylcyclopentadienyl hafnium (2-dimethylaminomethylphenyl) dimethylamide, n-butylcyclopentadienyl hafnium (2-dimethylaminomethylphenyl) dimethylamide, t-butylcyclopentadienyl hafnium (2-dimethylaminomethylphenyl) dimethylamide, pentamethylcyclopentadienyl hafnium (2-dimethylaminomethylphenyl) dimethylamide, cyclopentadienyl hafnium (2-dimethylaminomethylphenyl) diethylamide, methylcyclopentadienyl hafnium (2-dimethylaminomethylphenyl) diethylamide, ethylcyclopentadienyl hafnium (2-dimethylaminomethylphenyl) diethylamide, n-butylcyclopentadienyl hafnium (2-dimethylaminomethylphenyl) diethylamide, t-butylcyclopentadienyl hafnium (2-dimethylaminomethylphenyl) diethylamide, pentamethylcyclopentadienyl hafnium (2-dimethylaminomethylphenyl) diethylamide, cyclopentadienyl hafnium (2-dimethylaminomethylphenyl) (di-t-butylamide), methylcyclopentadienyl hafnium (2-dimethylaminomethylphenyl) (di-t-butylamide), ethylcyclopentadienyl hafnium (2-dimethylaminomethylphenyl) (di-t-butylamide), n-butylcyclopentadienyl hafnium (2-dimethylaminomethylphenyl) (di-t-butylamide), t-butylcyclopentadienyl hafnium (2-dimethylaminomethylphenyl) (di-t-butylamide), pentamethylcyclopentadienyl hafnium 2-dimethylaminomethylphenyl) (di-t-butylamide), cyclopentadienyl hafnium bis-(2-dimethylaminomethylphenyl), cyclopentadienyl hafnium methyl 2-dimethylaminobenzyl, cyclopentadienyl hafnium benzyl 2-dimethylaminobenzyl, cyclopentadienyl hafnium trimethylsilylmethyl 2-(dimethylamino)benzyl, methylcyclopentadienyl hafnium methyl 2-dimethylaminobenzyl, methylcyclopentadienyl hafnium benzyl 2-dimethylaminobenzyl, methylcyclopentadienyl hafnium trimethylsilylmethyl 2-(dimethylamino)benzyl, pentamethylcyclopentadienyl hafnium methyl 2-dimethylaminobenzyl, pentamethylcyclopentadienyl hafnium benzyl 2-dimethylaminobenzyl, pentamethylcyclopentadienyl hafnium trimethylsilylmethyl 2-(dimethylamino)benzyl.

Illustrative cyclic complexes, $A_3$, that may be employed in the practice of the present invention include: (tert-butylamido)dimethyl(tetramethyl-$\eta^5$-cyclopentadienyl) silane 2-(dimethylamino)benzyl titanium, (phenylamido) dimethyl(tetramethyl-$\eta^5$-cyclopentadienyl)silane 2-(dimethylamino)benzyl titanium, (tert-butylamido)

(tetramethyl-η⁵-cyclopentadienyl)-1,2-ethanediyl allyl titanium, (tert-butylamido)(tetramethyl-η⁵-cyclopentadienyl)-1,2-ethanediyl 2-(dimethylamino)benzyltitanium, (methylamido) (η⁵-cyclopentadienyl)-1,2-ethanediyl 2-(dimethylamino)benzyl titanium, (methylamido) (tetramethyl-η⁵-cyclopentadienyl)-1,2-ethanediyl allyl titanium, (phenylphosphido)(tetramethyl-η⁵-cyclopentadienyl)methylene 2-(dimethylaminomethyl)-phenyl titanium, (tert-butylamido)dibenzyl-(tetramethyl-η⁵-cyclopentadienyl)silane 2-(dimethylamino)benzyl titanium, (benzylamido)dimethyl(η⁵-cyclopentadienyl)silane 2-(dimethylaminomethyl)phenyl titanium, phenylphosphido)dimethyl(tetramethyl-η⁵-cyclopentadienyl)silane 2-(dimethylamino)benzyl titanium (III), (tert-butylamido)-dimethyl(η⁵-tetramethylcyclopentadienyl)silane allyl titanium, (phenylamido)-phenylmethyl(η⁵-tetrahydroindenyl)silane 2-(dimethylamino)benzyl titanium, (methylamido) cyclotetramethylene(η⁵-octahydrofluorenyl)silane 2-(dimethylamino)benzyl titanium, cyclopentadienylmethyl 2-(dimethylamino)benzyl titanium, (tert-butylamido)dimethyl(tetramethyl-η⁵-cyclopentadienyl)silane 2-(dimethylamino)benzyl zirconium, (phenylamido)dimethyl(tetramethyl-η⁵-cyclopentadienyl)silane 2-(dimethylamino)benzyl zirconium, (tert-butylamido) (tetramethyl-η⁵-cyclopentadienyl)-1,2-ethanediyl allyl zirconium, (tert-butylamido)(tetramethyl-η⁵-cyclopentadienyl)-1,2-ethanediyl 2-(dimethylamino)benzylzirconium, (methylamido)(η⁵-cyclopentadienyl)-1,2-ethanediyl 2-(dimethylamino)benzyl zirconium, (methylamido)(tetramethyl-η⁵-cyclopentadienyl)-1,2-ethanediyl allyl zirconium, (phenylphosphido)(tetramethyl-η⁵-cyclopentadienyl)methylene 2-(dimethylaminomethyl) phenyl zirconium, (tert-butylamido)dibenzyl(tetramethyl-η⁵-cyclopentadienyl)silane 2-(dimethylamino)benzyl zirconium, (benzylamido)dimethyl(η⁵-cyclopentadienyl) silane 2-(dimethylaminomethyl)phenyl zirconium, (phenylphosphido)dimethyl(tetramethyl-η⁵-cyclopentadienyl)silane 2-(dimethylamino)benzyl zirconium, (tert-butylamido)dimethyl(η⁵-tetramethylcyclopentadienyl)silane allyl zirconium, (phenylamido)phenylmethyl(η⁵-tetrahydroindenyl)silane 2-(dimethylamino)benzyl zirconium, and (methylamido) cyclotetramethylene(η⁵-octahydrofluorenyl)silane 2-(dimethylamino)benzyl zirconium.

Preferred cyclic complexes, A₃, are amidosilane- or amidoalkanediyl- compounds corresponding to the formula:

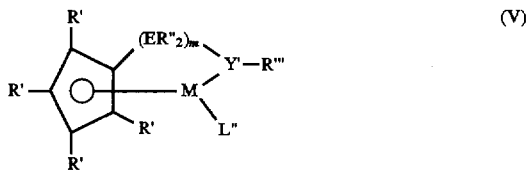

(V)

wherein

M, L", E, R', and R" are as previously defined;

Y' is nitrogen;

R'" is a group selected from silyl, hydrocarbyl and combinations thereof, said group or combination having up to 30 carbon or silicon atoms; and m is 1 or 2.

Preferably R'" is methyl, ethyl, propyl, butyl, pentyl, hexyl, (including where appropriate all isomers), cyclopentyl, cyclohexyl, norbornyl, benzyl, or phenyl.

In the most preferred embodiment —(ER"₂)ₘY'R'"— is an amidosilane or amidoalkane group of up to 30 nonhydrogen atoms, especially, (tert-butylamido)(dimethylsilyl), (methylamido)(dimethylsilyl), or (tert-butylamido)-1-ethane-2-yl.

Other complexes which are useful in the catalyst compositions of this invention will be apparent to those skilled in the art.

Highly preferably in complexes A₁, M is titanium and L is 2-dimethylaminobenzyl. Highly preferably in complexes A₂, M is titanium and L' is 2-dimethylaminobenzyl or allyl. Highly preferably in complexes A₃, M is titanium and L" is 2-dimethylaminobenzyl or allyl.

By the term "reducing agent" herein is meant a metal or compound which, under reducing conditions causes M to be reduced from the +4 oxidation state to the +3 oxidation state. Examples of suitable metal reducing agents are alkali metals, alkaline earth metals, lead and zinc, alloys of alkali metals or alkaline earth metals such as sodium/mercury amalgam and sodium/potassium alloy. Examples of suitable reducing agent compounds are sodium naphthalenide, potassium graphite, Grignard reagents, and the like. Most preferred reducing agents are the alkali metals or alkaline earth metals, especially magnesium.

By the term "reducing conditions" is meant the use of diluents and temperatures that allow the desired reduction to take place. Preferred temperatures are from 0° C. to 200° C., more preferably from 5° C. to 120° C. most preferably from 10° C. to 50° C. Preferred diluents are polar solvents, more preferably $C_{1-6}$ aliphatic ethers, most preferably tetrahydrofuran, 1,2-dimethoxyethane or diethyl ether.

The term "activating cocatalyst" as used herein refers to a secondary component that renders the metal complex catalytically effective or improves the catalytic effectiveness of the metal-containing complex as an addition polymerization catalyst. Examples of the activating cocatalysts for use herein include aluminum compounds containing an Al—O bond such as the alkylalumoxanes, especially methylalumoxane and isobutyl modified methylalumoxane; aluminum alkyls; aluminum halides; alkylaluminum halides; Lewis acids other than any of the foregoing list; and mixtures of the foregoing.

Preferred Lewis acids are those compounds corresponding to the formula: R""₃B, wherein R"" independently each occurrence is selected from hydrogen, silyl, hydrocarbyl, halohydrocarbyl, alkoxide, aryloxide, amide or combinations thereof, said R"" having up to 30 nonhydrogen atoms.

It is to be appreciated by those skilled in the art, that the above formula for the preferred Lewis acids represents an empirical formula, and that many Lewis acids exist as dimers or higher oligomers in solution or in the solid state. Other Lewis acids which are useful in the catalyst compositions of this invention will be apparent to those skilled in the art.

Preferred activating cocatalysts include trimethylaluminum, triisobutylaluminum, methylalumoxane, ethylalumoxane, chlorodiethylaluminum, dichloroethylaluminum, triethylboron, trimethylboron, triphenylboron and halogenated, especially fluorinated, triphenyl boron compounds.

Most highly preferred activating cocatalysts include triethylaluminum, methylalumoxane, and fluoro-substituted triaryl borons such as tris(4-fluorophenyl)boron, tris(2,4-difluorophenylboron), tris(3,5-bis(trifluoromethyl)phenyl) boron, tris(pentafluorophenyl)boron, pentafluorophenyldiphenylboron, and bis (pentafluorophenyl)phenylboron. Such fluoro-substituted triarylboranes Kay be readily synthesized according to techniques such as those disclosed in Marks, et al. J. Am. Chem. Soc., 113, 3623–3625 (199).

The catalyst can be utilized by forming the metal complex and where required combining the activating cocatalyst with the same in a diluent. The preparation may be conducted in the presence of one or more addition polymerizable monomers, if desired. Preferably, the catalysts are prepared at a temperature within the range from −100° C. to 300° C., preferably 0° C. to 250° C., most preferably 0° C. to 100° C. Suitable solvents include straight and branched-chain hydrocarbons such as isobutane, butane, pentane, hexane, heptane, octane, and mixtures thereof; cyclic and alicyclic hydrocarbons such as cyclohexane, cycloheptane, methylcyclohexane, methylcycloheptane, perfluorinated hydrocarbons such as perfluorinated $C_{4-10}$ alkanes and aromatic and alkyl-substituted aromatic compounds such as benzene, toluene and xylene. Suitable solvents also include liquid olefins which may act as monomers or comonomers including ethylene, propylene, butadiene, cyclopentene, 1-hexene, 3-methyl-1-pentene, 4-methyl-1-pentene, 1,4-hexadiene, 1-octene, 1-decene, styrene, divinylbenzene, 4-vinylcyclohexene, allylbenzene and vinyltoluene (including all isomers alone or in admixture). Preferred solvents are aliphatic hydrocarbons especially $C_5-C_{10}$ alkanes or cycloalkanes and mixtures thereof. Such a mixture is available commercially under the trade designation Isopar™E, available from Exxon Chemicals.

"Addition polymerizable monomers" usefully polymerized according to the present invention include, for example, ethylenically unsaturated monomers, cyclic olefins, acetylenic compounds, conjugated or nonconjugated dienes and polyenes, etc. Examples include $C_{2-20}$ olefins, styrene, halo- or hydrocarbyl substituted styrenes, divinylbenzene, 4-vinylcyclohexene, tetrafluoroethylene, vinylbenzocyclobutane, butadiene, isoprene, 1,4-hexadiene, cyclobutene, cyclopentene, cyclohexene, norbornene, ethylidene norbornene, and mixtures thereof. Preferred monomers include the $C_{2-10}$ α-olefins especially ethylene, propylene, isobutylene, 1-butene, 1-hexene, 4-methyl-1-pentene, styrene, and 1-octene.

In general, the polymerization may be accomplished at conditions well known in the prior art for Ziegler-Natta or Kaminsky-Sinn type polymerization reactions, that is, temperatures from 0° to 250° C. and pressures from atmospheric to 000 atmospheres (100 MPa). Suspension, solution, slurry, gas phase or other process condition may be employed if desired. The catalyst may be supported and such supported catalyst may be employed in the polymerizations of this invention. Preferred supports include alumina and silica.

The equivalent ratio of metal complex to activating cocatalyst (where employed) is preferably in a range from 1:0.5 to 1:10$^4$ more preferably from 1:0.75 to 1:10$^3$, most preferably 1:1 to 1:10. In most polymerization reactions the equivalent ratio of catalyst:polymerizable compound employed is from $10^{-12}$:1 to $10^{-1}$:1, more preferably from $10^{-9}$:1 to $10^{-4}$:1.

Surprisingly and contrary to teachings in the prior art, homogeneous, reduced, Group 4 metal catalysts have been discovered to be highly active addition polymerization catalysts.

Having described the invention the following examples are provided as further illustration thereof and are not to be construed as limiting. Unless stated to the contrary all parts and percentages are expressed on a weight basis.

EXAMPLES 1–58 i) Preparation Of Reduced Metal Complex(tert-butylamido)dimethyl(tetramethyl-η$^5$-cyclopentadienyl) silane 2-(dimethylamino)benzyl titanium, $(CH_3)_4C_5Si(CH_3)_2N\text{—}C(CH_3)_3)Ti(o\text{-}CH_2C_6H_4N(CH_3)_2)$

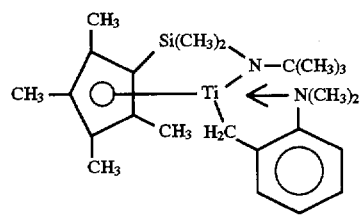

In the drybox, 1.65 g (4.45 mmol) of $TiCl_3(THF)_3$ and 2.29 g (4.46 mmol) of $(MgCl)_2((CH_3)_4C_5Si(CH_3)_2N\text{—}C(CH_3)_3)(THF)_2$ were mixed together in a 100 mL flask. Tetrahydrofuran (THF) (50 mL) was added to give a purple solution. After 15 minutes, 0.63 g (4.46 mmol) of o-LiCH$_2$C$_6$H$_4$N(CH$_3$)$_2$ was added. After 30 minutes, the volatile materials were removed under reduced pressure to yield a red-brown solid. Pentane (50 mL) was added, the solution was filtered, and the volume reduced to 40 mL. This concentrated solution was cooled to −30° C. Red crystals were isolated by filtration and dried under reduced pressure.

The electron paramagnetic resonance (EPR) spectrum of this material exhibited a single line at room temperature (g=1.974) and 2 lines at 77 K. The X-ray crystal structure had final cell parameters corresponding to a triclinic unit cell. Cell parameters were: a=9.922(4), b=14.366(9), c=9.857(5) (angstroms); α=104.35(6), B=111.69(4), Y=99.61(6); V=1212(1) (angstroms$^3$).

ii) Alternate preparation of (tert-butylamido)dimethyl (tetramethyl-η$^5$-cyclopentadienyl)silane 2-(dimethylamino) benzyl titanium—reduction of Ti(IV) complex.

In an argon filled glovebox, 0.990 g (2.69 mmol) of (tert-butylamido)dimethyl(tetramethyl-η$^5$-cyclopentadienyl)silane titanium dichloride (prepared by use of an organic halide oxidant according to the teachings of U.S. Ser. No. 702,475, filed May 20, 199, the teachings of which are incorporated herein by reference) and 0.389 g (2.76 mmol) of Li(o-CH$_2$(C$_6$H$_4$)N(CH$_3$)$_2$) were mixed together in a 100 mL flask. Pentane (75 mL) was added and the mixture stirred for 16 hours to provide an orange colored product. The mixture was filtered through a sintered glass frit. The solids were washed with pentane and the filtrates combined. Pentane solvent was removed under reduced pressure leaving a solid residue which was washed with cold pentane. The pentane wash was decanted from the residue and the product dried under reduced pressure giving 0.96 g. of an orange solid. $^1$H NMR analysis confirmed the product's identity as (tert-butylamido)dimethyl(tetramethyl-η$^5$-cyclopentadienyl)silane titanium 2-(dimethylamino)benzyl chloride. Yield was 76 percent.

The solid product (0.490 g, 1.05 mmole) obtained above was added to 50 ml of tetrahydrofuran. Magnesium powder (30 mg) was then added. The mixture was allowed to stir at 25° C. After 30 minutes the orange color of the solution changed to brown. After 4 hours the solvent was removed under reduced pressure. The solid residue was extracted with pentane (3×25 ml). The pentane extracts were filtered through a sintered glass frit, combined, and the pentane removed under reduced pressure to give 0.452 g (quantitative yield) of rose-purple microcrystalline solid, identified as (tert-butylamido)dimethyl(tetramethyl-η$^5$-cyclopentadienyl)silane 2-(dimethylamino)benzyl titanium by comparison of its cyclic voltamagram with that of the material obtained in Preparation i.

iii) Preparation of Reduced Metal Derivative(tert-butylamido)dimethyl(tetramethyl-η$^5$-cyclopentadienyl) silane allyl titanium (III), $((CH_3)_4C_5Si(CH_3)_2NC(CH_3)_3)Ti$ $(C_3H_5)$.

In the drybox, 0.30 g of TiCl$_3$(THF)$_3$ and 0.42 g of (MgCl)$_2$((CH$_3$)$_4$C$_5$Si(CH$_3$)$_2$N—C(CH$_3$)$_3$)(THF)$_2$ were mixed in a Schlenk tube. 20 mL of THF was added to give a purple solution. The Schlenk tube was sealed and removed to a Schlenk line, and the solution was cooled to –30° C. 0.81 mL of 1.0M allylmagnesium bromide was added by syringe. After 20 minutes, the solution was warmed to 0° C. and the volatile materials were removed under reduced pressure to yield a dark solid. While keeping the flask at 0° C. pentane (30 mL) was added, and the deep red solution was filtered, concentrated to ca. 5–7 mL, and cooled to –40° C. Red crystals were isolated by filtration and dried in 22 percent yield. The EPR spectrum of this material exhibited a single line at room temperature and 2 lines at 77K.

iv) Preparation of Reduced Metal Derivativebiscyclopentadienyl 2-(dimethylamino)benzyl titanium (III), Cp$_2$Ti(o-CH$_2$C$_6$H$_4$N(CH$_3$)$_2$).

This metal complex was prepared according to the procedure of *J. Am. Chem. Soc.* 100, 8068–8073 (1978) by reaction of stoichiometric amounts of biscyclopentadienyltitanium (III) chloride and 2-dimethylaminobenzyl lithium in diethylether.

v) Preparation of Reduced Metal Derivative(tert-butylamido)dimethyl(tetramethyl-η$^5$-cyclopentadienyl) silane 1,2,3-trimethylallyl titanium (III).

In a glovebox under an inert atmosphere, (tert-butylamido)dimethyl(tetramethyl-η$^5$-cyclopentadienyl) silanetitanium (IV) dichloride (0.500 g, 0.0014 mol) was dissolved in 3 ml of diethyl ether giving a yellow solution. To this solution was added 3-methyl-1,3-pentadiene (0.31 ml, 0.0027 mol) and i-PrMgCl (1.18 ml, 0.0045 mol). Gas evolution was noted and the color became red/purple. After 50 minutes the solvent was removed and the product dried.

Extraction with pentane (5×10 ml) and drying under reduce pressure gave the desired product as a red solid.

Polymerization

Several catalyst compositions were prepared by combining the metal complex and a cocatalyst in a stirred polymerization reactor. The cocatalysts used were tris (perfluorophenyl)borane (I), methylalumoxane (1M in toluene, available from Schering (AG) (II), trimethyl aluminum (III), triisobutylalaminum (IV), isobutyl modified methylalumoxane (1M in toluene, MMAO, type 3A, available from Texas Alkyls Corp.) (V), triethylaluminum (VI), phenyl bisperfluorophenyl borane (VII), and triphenyl borane (VIII). Accordingly, a 2 L stirred reactor was charged with the desired amounts of mixed alkane solvent (Isopar-E™ available from Exxon Chemicals Inc.) and 1-octene comonomer. The reactor was heated to the polymerization temperature, hydrogen was added by differential pressure expansion from a ~75 mL addition tank, and the reactor was saturated with ethylene to the desired pressure. Metal complex and cocatalyst (where used) were mixed in a drybox by syringing the desired amount of 0.0050 M metal complex solution (in Isopar-E™ or toluene) into a solution of the cocatalyst (in Isopar-E™ or toluene). This solution was then transferred to a catalyst addition tank and injected into the reactor. The same procedure was employed when no cocatalyst was employed excepting only the complex was added to the reactor. The polymerization was allowed to proceed for the desired time and the solution was removed from the reactor and quenched with isopropanol. A hindered phenol antioxidant (Irganox™ 1010, available from Ciba Geigy Corp.) was added and the polymers (linear low density polyethylenes) were air-dried for 16 hours and then dried in a reduced pressure oven. Results are contained in Table I.

TABLE I

| Ex. | Com- plex | Amt. (μmol) | Cocat- alyst | Amt. (μmol) | Solvent (g) | 1-Octene (g) | Ethylene (MPa) | H$_2$ (ΔkPa) | Temp (°C.) | Time (min) | Polymer (g) | Efficiency (g poly/g Ti) |
|---|---|---|---|---|---|---|---|---|---|---|---|---|
| 1 | i | 5.00 | I | 5.0 | 715 | 143 | 3.1 | 69 | 130 | 10 | 112.6 | 470,146 |
| 2 | i | 5.00 | I | 5.0 | 715 | 143 | " | 69 | 130 | 10 | 83.2 | 347,390 |
| 3 | i | 2.50 | I | 2.5 | 715 | 143 | " | 34 | 120 | 18 | 62.3 | 520,251 |
| 4 | i | 10.00 | II | 2940 | 715 | 143 | " | 340 | 130 | 15 | 54.7 | 114,196 |
| 5 | i | 10.00 | II | 184 | 715 | 143 | " | 340 | 130 | " | 22.5 | 46,973 |
| 6 | i | 10.00 | II | 2940 | 715 | 143 | " | 340 | 130 | " | 58.5 | 122,129 |
| 7 | i | 10.00 | IV | 1000 | 715 | 143 | " | 340 | 130 | " | 23.7 | 49,478 |
| 8 | i | 10.00 | II | 1470 | 787 | 72 | " | 34 | 160 | " | 17.8 | 37,161 |
| 9 | i | 10.00 | II | 2940 | 787 | 72 | " | 0 | 175 | " | 13.6 | 28,392 |
| 10 | i | 10.00 | II | 7350 | 715 | 143 | " | 340 | 130 | " | 53.7 | 112,109 |
| 11 | iii | 10.00 | II | 588 | 715 | 143 | " | 340 | 130 | " | 37.8 | 78,914 |
| 12 | iii | 10.00 | II | 441 | 715 | 143 | " | 340 | 130 | " | 23.1 | 48,225 |
| 13 | i | 0.50 | I | 1.5 | 740 | 118 | 3.4 | 170 | 100 | " | 62.2 | 2,597,077 |
| 14 | i | 1.50 | I | 3.0 | 788 | 70 | " | 90 | 160 | " | 20.0 | 285,317 |
| " | i | 1.00 | I | 3.0 | 740 | 118 | " | 340 | 140 | " | 30.7 | 640,919 |
| 16 | i | 1.00 | I | 3.0 | 740 | 118 | " | 0 | 140 | " | 18.7 | 390,397 |
| 17 | i | 0.75 | I | 1.5 | 691 | 167 | " | 90 | 120 | " | 45.5 | 1,266,527 |
| 18 | i | 0.75 | I | 1.5 | 788 | 70 | " | 260 | 120 | " | 44.8 | 1,247,042 |
| 19 | i | 0.75 | I | 3.0 | 691 | 167 | " | 90 | 120 | " | 43.2 | 1,202,505 |
| 20 | i | 1.00 | I | 3.0 | 740 | 118 | " | 170 | 140 | " | 17.2 | 359,081 |
| 21 | i | 1.50 | I | 6.0 | 788 | 70 | " | 260 | 160 | " | 12.4 | 172,582 |
| 22 | i | 0.75 | I | 1.5 | 788 | 70 | " | 90 | 120 | " | 41.6 | 1,157,968 |
| 23 | i | 1.00 | I | 3.0 | 740 | 118 | " | 170 | 140 | " | 10.1 | 210,856 |
| 24 | i | 0.75 | i | 3.0 | 788 | 70 | " | 90 | 120 | " | 45.2 | 1,258,177 |
| 25 | i | 1.00 | i | 3.0 | 740 | 118 | " | 170 | 140 | " | 16.3 | 340,292 |
| 26 | i | 1.00 | I | 3.0 | 740 | 118 | 3.4 | 170 | 140 | 15 | 12.6 | 263,048 |
| 27 | i | 10.00 | I | 30.0 | 740 | 118 | " | " | 180 | " | 12.5 | 26,096 |
| 28 | i | 1.00 | I | 3.0 | 837 | 21 | " | " | 140 | " | 43.0 | 897,704 |
| 29 | i | 1.00 | I | 3.0 | 740 | 118 | " | " | 140 | " | 27.9 | 582,463 |
| 30 | i | 0.75 | I | 3.0 | 691 | 167 | " | 260 | 120 | " | 39.4 | 1,096,729 |
| 31 | i | 1.00 | I | 3.0 | 740 | 118 | " | 170 | 140 | " | 20.2 | 421,712 |
| 32 | i | 1.50 | I | 6.0 | 691 | 167 | " | 91 | 160 | " | 5.1 | 70,981 |
| 33 | i | 1.50 | I | 3.0 | 691 | 167 | " | 91 | 160 | " | 5.8 | 80,724 |

TABLE I-continued

| Com- Ex. plex | Amt. (μmol) | Cocat- alyst | Amt. (μmol) | Solvent (g) | 1-Octene (g) | Ethylene (MPa) | $H_2$ (ΔkPa) | Temp (°C.) | Time (min) | Polymer (g) | Efficiency (g poly/g Ti) |
|---|---|---|---|---|---|---|---|---|---|---|---|
| 34 i | 1.00 | I | 3.0 | 644 | 215 | " | 170 | 140 | " | 13.8 | 288,100 |
| 35 i | 1.50 | I | 3.0 | 691 | 167 | " | 260 | 160 | " | 8.4 | 116,910 |
| 36 i | 1.00 | I | 5.0 | 740 | 118 | " | 170 | 140 | " | 17.0 | 354,906 |
| 37 i | 1.50 | I | 6.0 | 691 | 167 | " | 260 | 160 | " | 6.9 | 96,033 |
| 38 i | 0.75 | I | 1.5 | 691 | 167 | " | 260 | 120 | " | 50.9 | 1,416,841 |
| 39 i | 1.50 | I | 3.0 | 788 | 70 | " | 260 | 160 | " | 7.3 | 101,601 |
| 40 i | 0.75 | I | 3.0 | 788 | 70 | " | 260 | 120 | " | 29.7 | 826,722 |
| 41 i | 1.00 | I | 1.0 | 740 | 118 | " | 170 | 140 | " | 7.8 | 162,839 |
| 42 i | 1.50 | I | 6.0 | 788 | 70 | " | 90 | 160 | " | 2.9 | 40,362 |
| 43 i | 1.00 | I | 3.0 | 740 | 118 | " | 170 | 140 | " | 13.3 | 277,662 |
| 44 i | 2.50 | III | 2.5 | 740 | 118 | " | " | 120 | " | 1.6 | 13,361 |
| 45 i | 2.50 | III | 5.0 | 740 | 118 | " | " | 120 | " | .7 | 5,846 |
| 46 i | 2.50 | III | 7.5 | 740 | 118 | " | " | 120 | " | 0.7 | 5,846 |
| 47 i | 2.50 | IV | 7.5 | 740 | 118 | " | " | 120 | " | 0.5 | 4,175 |
| 48 i | 2.50 | V | 37.5 | 740 | 118 | " | " | 120 | " | 3.3 | 20,577 |
| 49 i | 2.50 | VI | 3.7 | 740 | 118 | " | " | 120 | " | 8.2 | 68,476 |
| 50 i | 2.50 | VI | 7.5 | 740 | 118 | " | " | 120 | " | 8.9 | 74,322 |
| 51 i | 2.50 | VI | 25.0 | 740 | 118 | 3.4 | 170 | 120 | 15 | 9.1 | 75,992 |
| 52 i | 2.50 | VI | 75.0 | 740 | 118 | " | " | " | " | 5.7 | 47,599 |
| 53 iv | 2.50 | I | 7.5 | 740 | 118 | " | " | " | " | 36.3 | 303,132 |
| 54 ii | 2.00 | I | 30.0 | 740 | 118 | " | " | 140 | " | 112.4 | 1,174,000 |
| 55 ii | " | VII | 3.0 | " | " | " | " | 140 | " | 122.4 | 1,277,000 |
| 56 ii | " | — | 0.0 | " | " | " | " | " | " | 72.3 | 755,000 |
| 58 v | 0.75 | I | 0.75 | 708 | 150 | " | " | 120 | " | 68.8 | 1,915,000 |

EXAMPLE 58

Preparation of (phenylamido)dimethyl(tetramethyl-$\eta^5$-cyclopentadienyl)silane 2-(dimethylamino)benzyl titanium chloride In an argon filled glove box, 0.55 g (1.29 mmol) of (phenylamido)dimethyl(tetramethyl-$\eta^5$-cyclopentadienyl) silane titanium dichloride (prepared according to example 89 of U.S. Ser. No. 545,403 filed Jul. 3, 1990) and 0.18 g (1.3 mmol) of 2-(dimethylamino)benzyl lithium were slurried in ~75 mL of pentane. The mixture turned from yellow to red after ~16 hours. The mixture was filtered and the solids were extracted with diethyl ether. The pentane and ether fractions were devolatilized under reduced pressure. $^1$H NMR analysis confirmed the product's identity from both fractions as (phenylamido)dimethyl(tetramethyl-$\eta^5$-cyclopentadienyl)silane titanium 2-(dimethylamino)benzyl chloride. Total yield was 0.33 g, 53 percent.

Preparation of (phenylamido)dimethyl(tetramethyl-$\eta^5$-cyclopentadienyl)silane-2-(dimethylamino)benzyl titanium In an argon filled glove box 16 mg of magnesium powder was added to 0.33 g (0.68 mmol) of (phenylamido)dimethyl (tetramethyl-$\eta^5$-cyclopentadienyl)silane 2-(dimethylamino) benzyl titanium chloride in ~40 mL of tetrahydrofuran (THF). After stirring for 6 hours the THF was removed under reduced pressure. The solid residue was extracted with pentane. The pentane extracts were filtered and combined and the pentane solvent removed under reduced pressure to give 0.29 g (94 percent yield) of (phenylamido)dimethyl (tetramethyl-$\eta^5$-cyclopentadienyl)silane-2-(dimethylamino) benzyl titanium, characterized by cyclic voltametry.

We claim:

1. An addition polymerization catalyst comprising in combination:

a metal complex corresponding to the formula:

$Cp_2ML$, wherein

Cp independently each occurrence is a cyclopentadienyl group, or a hydrocarbyl, silyl, halo, halohydrocarbyl, hydrocarbylmetalloid or halohydrocarbylmetalloid substituted derivative of said cyclopentadienyl group, said Cp group containing up to 50 nonhydrogen atoms, and optionally both Cp groups may be joined together by a bridging group;

M is a metal of Group 4 of the periodic Table of the Elements in the $^+3$ oxidation state;

L is a monovalent anionic ligand selected from the group consisting of: alkyl, cycloalkyl, aryl, silyl, amido, phosphido, alkoxy, aryloxy, sulfido groups and mixtures thereof, and being further substituted with an amine, phosphine, ether, or thioether-containing substituent able to form a coordinate-covalent bond or chelating bond with M; said ligand having up to 50 nonhydrogen atoms;

and an activating cocatalyst.

2. A catalyst as claimed in claim 1 wherein M is titanium.

3. A catalyst as claimed in claim 1, wherein L is 2-(dimethylamino)benzyl.

4. A catalyst according to claim 1 wherein the ratio of metal complex to activating cocatalyst is from 1:0.01 to 1:10$^6$.

5. A catalyst as claimed in claim 1 wherein the activating cocatalyst is selected from the group consisting of alkylalumoxanes; aluminum alkyls; aluminum halides; alkylaluminum halides; Lewis acids other than any of the foregoing; and mixtures thereof.

6. A catalyst as claimed in claim 5, wherein the activating cocatalyst is tris(4-fluorophenyl)boron, tris(2,4-difluorophenylboron), tris(3,5-bis(trifluoromethyl)phenyl) boron, tris(pentafluorophenyl)boron, pentafluorophenyl diphenylboron, triphenyl boron or bis(pentafluorophenyl) phenylboron.

7. A catalyst as claimed in claim 5, wherein the complex is biscyclopentadienyl-2-(dimethylamino)benzyltitanium (III), and the cocatalyst is tris(perfluorophenyl)borane.

* * * * *